US007851158B2

(12) United States Patent
McKernan

(10) Patent No.: US 7,851,158 B2
(45) Date of Patent: Dec. 14, 2010

(54) ENRICHMENT THROUGH HETERODUPLEXED MOLECULES

(75) Inventor: Kevin J. McKernan, Marblehead, MA (US)

(73) Assignee: Applied Biosystems, LLC, Carlsbad, CA (US)

(*) Notice: Subject to any disclaimer, the term of this patent is extended or adjusted under 35 U.S.C. 154(b) by 0 days.

(21) Appl. No.: 11/966,720

(22) Filed: Dec. 28, 2007

(65) Prior Publication Data

US 2008/0274466 A1 Nov. 6, 2008

Related U.S. Application Data

(60) Provisional application No. 60/877,813, filed on Dec. 29, 2006.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. .................. 435/6; 435/91.2; 536/22.1; 536/23.1; 536/24.3

(58) Field of Classification Search .................. 435/6, 435/91.2; 536/22.1, 23.1, 24.3
See application file for complete search history.

(56) References Cited

U.S. PATENT DOCUMENTS

| | | | |
|---|---|---|---|
| 4,946,773 | A | 8/1990 | Maniatis et al. |
| 5,556,750 | A | 9/1996 | Modrich et al. |
| 5,824,471 | A * | 10/1998 | Mashal et al. ............... 435/6 |
| 5,869,245 | A * | 2/1999 | Yeung ........................ 435/6 |
| 6,054,276 | A | 4/2000 | Macevicz |
| 7,198,894 | B2 * | 4/2007 | Barany et al. ............... 435/6 |
| 7,247,428 | B2 * | 7/2007 | Makrigiorgos ............. 435/6 |
| 2002/0146732 | A1 | 10/2002 | Padgett et al. |
| 2003/0022215 | A1 * | 1/2003 | Makrigiorgos ............. 435/6 |
| 2003/0114650 | A1 * | 6/2003 | Cheung et al. ............ 536/23.1 |
| 2003/0157477 | A1 * | 8/2003 | Gyuris ....................... 435/5 |
| 2004/0142433 | A1 | 7/2004 | Padgett et al. |
| 2006/0024681 | A1 | 2/2006 | Smith |
| 2009/0068659 | A1 * | 3/2009 | Taylor et al. ............... 435/6 |

FOREIGN PATENT DOCUMENTS

| | | |
|---|---|---|
| EP | 1681358 | 7/2006 |
| EP | 07870084 | 5/2010 |
| WO | WO-01/05800 | 1/2001 |
| WO | WO 2008/083327 | 6/2009 |

OTHER PUBLICATIONS

Bhattacharyya et al. Model for the interaction of DNA junctions and resolving enzymes. Journal of Molecular Biology 221(4), 1191-207(1991).*
Kleff t al Initiation of heteroduplex-loop repair by T4-encoded endonuclease VII in vitro EMBO Journal 7(5), 1527-1535 (1988).*
Kosak et al, Large-scale preparation of T4 endonuclease VII from over-expressing bacteria. European Journal of Biochemistry 194(3), 779-784 (1990).*
Lishanski et al., Mutation detection by Mismatch binding protein, MutS, in amplified DNA : Application to the cystic fibrosis gene. PNAS 91 : 2674-2678 (1994).*
Mizuuchi et al. T4 endonuclease VII cleaves Holliday structures. Cell 29(2), 357-365 (1982).*
Oleykowski et al., Mutation detection using a novel plant endonuclease. Ncleic Acids Research 26 (20) : 4597-4602 (1998).*
Solaro et al. Endonuclease VII of phage T4 triggers mismatch correction in vitro Journal of Molecular Biology 230(3), 868-877 (1993).*
West S.C., Enzymes and Molecular Mechanisms of Genetic Recombination. Annual Reviews in Biochemistry 61 : 603-640 (1992).*
White et al., Detecting single base substitutions as heteroduplex polymorphisms. Genomics 12(2) : 301-306(1992).*
Authorized Officer, Ethan Whisenant, Ph.D., PCT International Search Report, Jul. 28, 2008, 3 pages.
Cotton et al., "Reactivity of Cytosine and Thymine in Single-Base-Pair Mismatches with Hydroxylamine and Osmium Tetroxide and its Application to the Study of Mutations", *PNAS*, vol. 58, Jun. 1988, pages. 4397-4401.
Youil et al., "Screening for Mutations by Enzyme Mismatch Cleavage with T4 Endonuclease VII", *PNAS*, vol. 92, Jan. 1995, pp. 4397-4401.
Youil et at., "Screening for Mutations by Enzyme Mismatch Cleavage with T4 Endonuclease VII", *Proc.Natl. Acad. Sci. USA*, vol. 92, pp. 87-91, Jan. 1995.
Baum, L., et al., "Developing the use of mismatch binding proteins for discovering rare somatic mutations", *Molecular and Cellular Probes*, Elsevier, vol. 19, No. 3, Jun. 1, 2005, 163-168.
Golz, S., et al., "Enzymatic mutation detection: enrichment of heteroduplexes from hybrid DNA mixtures by cleavage-deficient GST-tagged endonuclease VII",*Nucleic Acids Research*, vol. 27, No. 15, 1999, 1-4.

* cited by examiner

*Primary Examiner*—Ethan Whisenant

(57) ABSTRACT

The present invention relates to the enrichment of specific target sequences. Enrichment can be achieved through the formation of a heteroduplex that includes the specific target sequence and then the specific cleavage of the heteroduplex. A binding moiety is then added to the cleaved heteroduplex, allowing for the subsequent manipulation of the specific target sequence in the heteroduplex.

37 Claims, 11 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(20)
<223> OTHER INFORMATION: n is a, c, g, or t

<400> SEQUENCE: 1
ggccaaggcg gatgtacgnn                                                      20

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (18)..(19)
<223> OTHER INFORMATION: n is a, c, g, or t

<400> SEQUENCE: 2
cgtacaccgc cttggccnn                                                       19

<210> SEQ ID NO 3
<211> LENGTH: 41
<212> TYPE: DNA
<213> ORGANISM: Artificial Sequence
<220> FEATURE:
<223> OTHER INFORMATION: Synthetic DNA

<400> SEQUENCE: 3
ccactacgcc tccgctttcc tctctatggg cagtcggtga t                              41

<210> SEQ ID NO 4
<211> LENGTH: 43
<212> TYPE: DNA
<213> ORGANISM: Artificial Sequence
<220> FEATURE:
<223> OTHER INFORMATION: Synthetic DNA

<400> SEQUENCE: 4
```

-continued

```
atcaccgact gcccatagag aggaaagcgg aggcgtagtg gtt          43

<210> SEQ ID NO 5
<211> LENGTH: 23
<212> TYPE: DNA
<213> ORGANISM: Artificial Sequence
<220> FEATURE:
<223> OTHER INFORMATION: Synthetic DNA

<400> SEQUENCE: 5
ctgccccggg ttcctcattc tct                                23

<210> SEQ ID NO 6
<211> LENGTH: 25
<212> TYPE: DNA
<213> ORGANISM: Artificial Sequence
<220> FEATURE:
<223> OTHER INFORMATION: Synthetic DNA

<400> SEQUENCE: 6
agagaatgag gaacccgggg cagtt                              25

<210> SEQ ID NO 7
<211> LENGTH: 28
<212> TYPE: DNA
<213> ORGANISM: Artificial Sequence
<220> FEATURE:
<223> OTHER INFORMATION: Synthetic DNA

<400> SEQUENCE: 7
ccactacgcc tccgctttcc tctctatg                           28

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA

<400> SEQUENCE: 8
ctgccccggg ttcctcattc t                                  21
```

ENRICHMENT THROUGH HETERODUPLEXED MOLECULES

FIELD

Methods and compositions for the enrichment of nucleic acids are provided. Particular embodiments relate to enriching nucleic acid sequences through the formation of heteroduplex molecules.

INTRODUCTION

Various enzymes are capable of cutting or nicking at mismatched base pairs in heteroduplexes of nucleic acid sequences. The mismatched base pair can be used as a restriction cite, allowing for the relatively selective cutting of any hybridized set of nucleic acid sequences that contain such a mismatch, at or near the mismatched base pairs. By creating a particular mismatch using a particular set of paired nucleic acid sequences, it is possible effectively add a restriction site into any set of hybridized nucleic acid sequences. Thus, it is possible to obtain mismatch dependent cutting of nucleic acid sequences. In some situations, this mismatch dependent cleavage can be used to identify where a mismatch is by running these cleaved products on a gel. By noting the size of the fragments, it is possible to locate the site of the initial mismatch.

SUMMARY

In some aspects a method for the enrichment of a nucleic acid sequence is provided. The method includes forming a heteroduplex including a first nucleic acid sequence and a second nucleic acid sequence. The heteroduplex includes at least one mismatched base pair between the first nucleic acid sequence and the second nucleic acid sequence. The method can include circularizing the heteroduplex to form a circularized heteroduplex (CHET), preferentially cutting the CHET to form a duplex using an enzyme that recognizes the mismatched base pair, associating a binding moiety into the duplex to form a binding moiety duplex. In some embodiments the binding moiety is associated with a nucleic acid sequence so as to form a binding moiety nucleic acid sequence (BMNAS). In some embodiments the BMNAS includes two nucleic acid sequences hybridized to one another and a binding moiety. The method further involves selecting the binding moiety, thereby enriching those nucleic acids associated with the binding moiety. In some embodiments, the selection can be achieved by using a purifying moiety that binds to the binding moiety, thereby enriching the second nucleic acid sequence.

In some aspects the preferential cutting occurs at a predetermined location relative to the mismatched base pair. In some aspects, Endo V is used to cut the CHET. In some aspects, the preferential cutting occurs at a location one base pair away from the mismatched base pair. In some aspects, the method further includes forming a nucleic acid homoduplex and circularizing the homoduplex to form a circularized homoduplex (CHOM). The CHOM does not contain a mismatched base pair, and the forming and circularizing of the homoduplex is performed together with the forming and circularizing of the heteroduplex. In some aspects, the step of preferentially cutting the CHET does not result in a significant cutting of the CHOM. In some aspects, the BMNAS further includes a first restriction site. in some aspects, the BMNAS further includes a second restriction site and each of the restriction sites is located at or near opposite ends of the nucleic acid sequence. In some aspects, the binding moiety includes biotin. In some aspects, more than one type of BMNAS is used, and the BMNASs can have degenerate 5' and 3' ends. In some aspects, at least 16 BMNASs are used, each BMNAS having a different 5' and 3' end sequence combination. In some aspects, at least 1024 BMNASs are used, each BMNAS having a different 5' and 3' end sequence combination. In some aspects, there is an additional step of cutting the binding moiety duplex to form a cut binding moiety duplex (CBMD). In some aspects, the cutting is controlled by restriction sites within the BMNAS. In some aspects, the cutting occurs by a Type IIs or a Type III cutter. In some aspects, the cutting occurs approximately 30 base pairs away from a restriction site for the cutting. In some aspects, there is the additional step of identifying the second nucleic acid sequence. In some aspects, there is an additional step of identifying the mismatched base pair. In some aspects, identification can occur by sequencing the mismatched base pair. In some aspects there is an additional step of adding a first adapter to a first end of the CBMD. In some aspects there is an additional step of adding a second adapter to a second end of the CBMD. The first and second adapters do not have to be the same and can be different. In some aspects, the first adapter is a first primer site and the second adapter is a second primer site. In some aspects there is an additional step of using the first and second primer sites to amplify a sequence between the two primer sites. In some aspects, the amplification is achieved through emulsion PCR. In some aspects there is an additional step of sequencing the amplified sequence. In some aspects, the method is performed in vitro. In some aspects, the enrichment of the second nucleic acid sequence occurs through the binding of the binding moiety to the purifying moiety. In some aspects there is an additional step of forming a second CHET, wherein the first CHET and the second CHET have different mismatched base pairs. In some aspects, at least 100 CHETs are formed, each with a different mismatched base pair. In some aspects, at least 1000 CHETs are formed, each with a different mismatched base pair. In some aspects, the first nucleic acid includes DNA. In some aspects, the second nucleic acid includes DNA. In some aspects, there is more of the first nucleic acid sequence than the second nucleic acid sequence during the formation of the heteroduplex. In some aspects, the ratio of first to second nucleic acid sequence to the second nucleic acid sequence present during the formation of the heteroduplex is no less than 5:1. In some aspects, the ratio of first to second nucleic acid sequences present during the formation of the heteroduplex is no less than 100:1. In some aspects, the ratio of first to second nucleic acid sequences present during the formation of the heteroduplex is no less than 1000:1.

In some aspects, a method for the enrichment of a nucleic acid sequence is provided. In some embodiments, the method includes providing a sample with a first nucleic acid sequence (FNAS) and a second nucleic acid sequence (SNAS), providing two primers suitable for hybridization on complementary strands of the FNAS and the SNAS, providing a polymerase, combining the sample, the primers, and the polymerase to form a polymerase chain reaction mixture, subjecting the polymerase chain reaction mixture to one or more polymerase chain reaction cycles to create a polymerase chain reaction extension product, denaturing the polymerase chain reaction extension product to separate a FNAS and a SNAS, and annealing the polymerase chain reaction extension product to form a heteroduplex including the FNAS and the SNAS and to form a homoduplex including the FNAS. The method can further include circularizing the heteroduplex to form a circularized heteroduplex (CHET), circularizing the homoduplex to form a circularized homoduplex (CHOM), providing an endonuclease that preferentially cuts the heteroduplex at a location one base away from mismatched base pairs, wherein said cutting of the heteroduplex is preferential over the cutting of the homoduplex, combining the CHET, the CHOM, and the endonuclease to form an endonuclease cleavage reaction mixture, incubating the endonuclease cleavage reaction mixture so that the endonuclease preferentially cuts the CHET at a location one base away from a mismatched base pairs, and providing a plurality of binding moiety nucleic acid sequences (BMNAS). The BMNASs can have a double stranded nucleic acid sequence, biotin associated with the double stranded nucleic acid sequence, two EcoP15I restriction sites on each nucleic acid sequence, wherein one restriction site is located near or at the 3' end of one nucleic acid strand and the second restriction site is located near or at the 5' end of the nucleic acid strand, and degenerate ends on each end of each nucleic acid sequence. The method can further include ligating the BMNAS into the duplex to form a binding moiety duplex, cutting the binding moiety duplex using EcoP15I, and concentrating the binding moiety duplex by using magnetic beads. The method can further include cutting the concentrated binding moiety duplex by using EcoP15I to form a cut binding moiety duplex (CBMD), adding a first adapter to a first end of the CBMD, and adding a second adapter to a second end of the CBMD. The first and second adapters can be different. The method can further include performing emulsion PCR to amplify the CBMD using the first and second adapters as priming sites and performing a highly parallel non-electrophoretic sequencing technique on the CBMD to identify the mismatched base pair.

These and other features of the present teachings are set forth herein.

BRIEF DESCRIPTION OF THE DRAWINGS

One of ordinary skill in the art will understand that the drawings, described below, are for illustration purposes only. The drawings are not intended to limit the scope of the present teachings in any way.

DESCRIPTION OF VARIOUS EMBODIMENTS

The present teachings are generally directed towards compositions and methods for increasing the relative amount of a particular nucleic acid sequence or section thereof. In many situations, a biological sample, such as a cell or a tissue sample from a biopsy, can contain a variety of highly related nucleic acid sequences. While traditional molecular biology techniques are often adequate to identify the common nucleic acid sequences in the sample, they frequently miss those nucleic acid sequences that are relatively rare, as the presence of the rare nucleic acid sequences are hidden by the presence of more common similar nucleic acid sequences. For example, in a tissue biopsy of a patient, while the majority of cells may contain a gene having a wild-type sequence, some cells, for example cancer cells, contain the same gene with a variation in the sequence. If the cancer cells are in a small minority of the cells tested, the smaller population of variant nucleic acid sequences, and thus the cancer itself, can go undetected.

Figure 1:
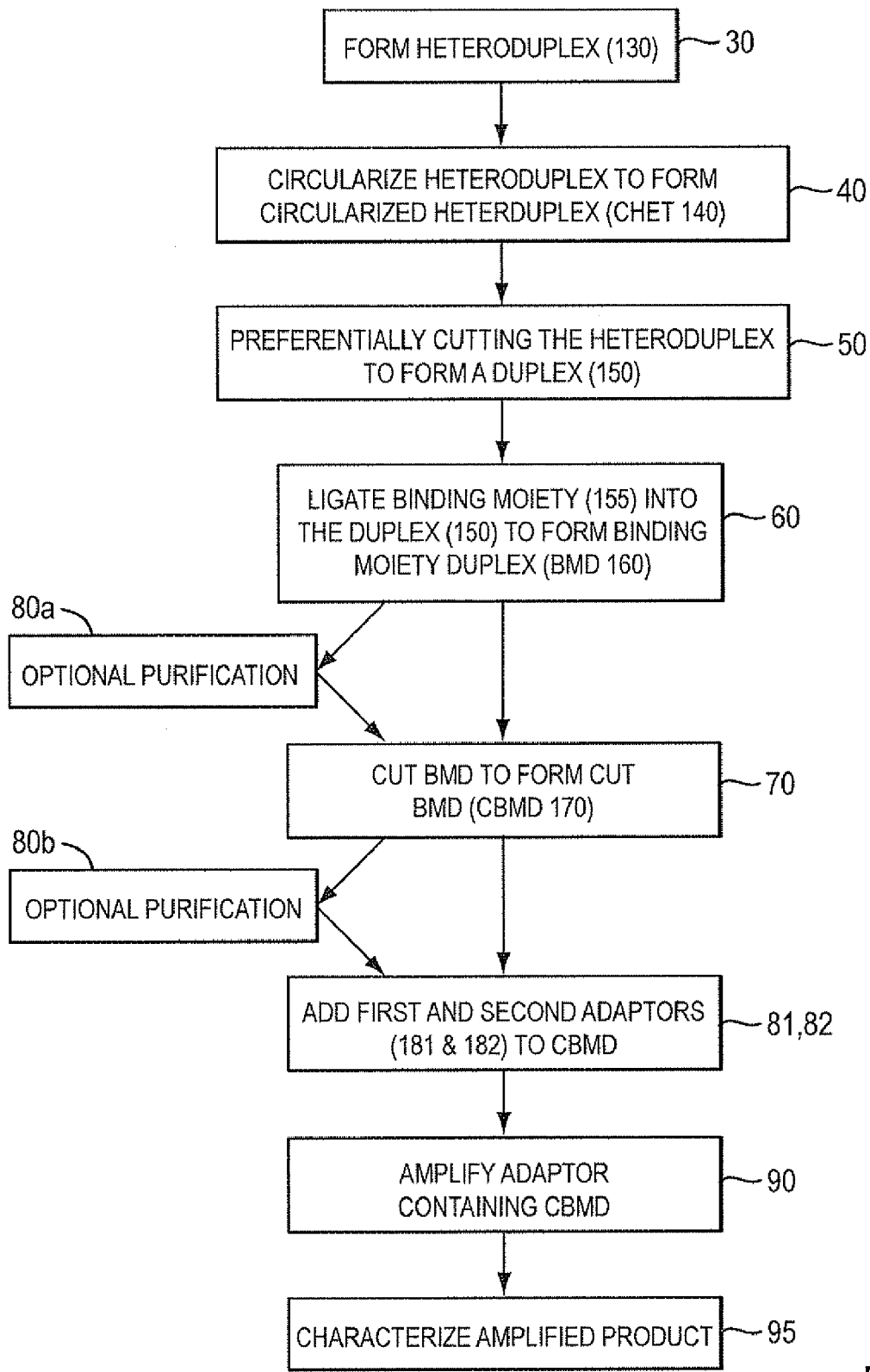
FIG. 1 depicts a flow chart demonstrating one embodiment for enriching a nucleic acid sequence.

Some of the present embodiments involve an assay that enriches for a relatively rare nucleic acid sequence(s). One such embodiment is generally outlined in FIG. 1. In FIG. 1, a heteroduplex 130 is formed in step 30, for example, by melting two different homoduplexes and allowing the sequences to reanneal. The heteroduplex includes a mismatch between a first nucleic acid sequence and a second nucleic acid sequence. The heteroduplex is circularized to form a circularized heteroduplex (CHET 140) in step 40. Next, the heteroduplex is selectively cut in a mismatch dependent manner to form a duplex (150) in step 50. This cutting can occur near the base pair mismatch. Following this, a binding moiety 155 is ligated into the duplex 150 to form a binding moiety duplex 160 in step 60. At this point, the initial heteroduplex can be purified through the use of the binding moiety in step 80a.

As will be appreciated by one of skill in the art, the above method will allow for the effective insertion of a binding moiety (BM) into a heteroduplex of nucleic acid sequences, thereby permtting one to manipulate the heteroduplex and allowing one to increase its relative concentration. Additionally, while the BM will be inserted into a heteroduplex nucleic acid sequence, it will not be effectively inserted into homoduplex moieties. Thus, the method allows selective insertion of the BM into heteroduplexes over homoduplexes. By forming a heteroduplex that includes the nucleic acid sequence that one wishes to enrich for, and forming homoduplexes with those sequences one does not wish to amplify, one can use the embodiment to selectively enrich one population of nucleic acids over another population.

Furthermore, as shown in of FIG. 1, the nucleic acid sequences in the heteroduplex can be characterized 95, thereby identifying the nucleic acids involved in the base pair mismatch. Instead of purifying the heteroduplex 80a, as described above, the BMD can be cut directly to form a cut BMD (CBMD 170) in step 70, then purified or enriched in step 80b. Following this purification/enrichment, the nucleic acid comprising the point mutation can be amplified in a variety of ways. In some embodiments, first and second adapters 181 and 182 are added to the CBMD in steps 81 and 82. PCR amplification of the CBMD can then be performed using the adapters as priming sites in step 90. The amplified PCR product can be characterized 95 through sequencing. Thus, both sequences of the nucleic acids of the heteroduplex to be determined. In this way, the relative amount of a nucleic acid sequence can be increased. In addition, it is possible to identify how the nucleic acid sequence differed from another nucleic acid sequence (i.e., what nucleic acids were involved in the mismatch). As will be appreciated by one of skill in the art, the ability to identify the differences between sequences that are otherwise very similar can have great benefit, especially when one of the sequences is present in a relatively small percent. While this section has briefly outlined some of the general concepts behind certain of the presently disclosed embodiments, a more detailed account is presented following the next section. The following section provides a set of definitions of the terms used in the specification.

DEFINITIONS

"First Nucleic Acid Sequence" (FNAS) means a nucleic acid which is to be compared to one or more other nucleic acid sequences. The FNAS can be of any length or sequence. Examples of a FNAS include genes of interest, for example, those genes that are associated with a disease or disorder. In some embodiments, the FNAS is more abundant in a sample than the SNAS. In some embodiments, the FNAS is the "control sequence," meaning that it is a known sequence against which the presence or characteristics of another sequence are to be tested, although this can be reversed. As will be appreciated by one of skill in the art, a "nucleic acid sequence" is broader than simply a gene or a nucleic acid sequence that encodes for a protein.

"Second Nucleic Acid Sequence" (SNAS) means a nucleic acid which is to be characterized and/or enriched. The SNAS can be of any length or sequence. SNAS can include genes and nucleic acid sequences of interest, that can be, for example, associated with a disease or disorder. In some embodiments, the SNAS is less abundant than the FNAS). In some embodiments, the SNAS is the target sequence, although this can be reversed.

As noted herein, the FNAS and SNAS are capable of binding to each other via Watson-crick base pairing to form a heteroduplex. As will be appreciated by one of skill in the art, the FNAS and SNAS will also have at least one (although more may be present in some embodiments) base pair difference between them. The difference can be, for example, an insertion, deletion, and be more than one base pair long. Also, in some embodiments if the FNAS and SNAS are sufficiently similar an initial PCR amplification can be carried out using the same set of PCR primers to amplify the FNAS and the SNAS. In some embodiments, the FNAS differs from the SNAS by at least one base pair, e.g., 1-2, 2-3, 3-4, 4-6, 6-10, 10-15, 15-30, 30-60, 60-100, 100-200, or more base pairs. As long as a heteroduplex can be formed with the FNAS and SNAS and circularized, any size difference between the two is possible. As noted herein, in some embodiments, the FNAS and SNAS differ by only one base. Thus, in some embodiments, there is only a single nucleotide that is different between the two sequences. As used herein, when it is said that the FNAS and SNAS are hybridized, it is understood that this does not mean that they are completely hybridized. In particular, the bases involved in the base pair mismatch are not hybridized together. As noted herein, in some embodiments, the amount of FNAS in the sample or during the formation of the heteroduplex is greater than the amount of the SNAS. In some embodiments, the ratio of FNAS:SNAS is no less than (meaning there is at least this amount of FNAS compared to SNAS) 1:1, 5:1, 10:1, 100:1, 100:1, 10,000:1, 100,000:1, or 1,000,000:1.

The term "species" when used with FNAS and/or SNAS denotes that different sequences, which need not be complementary or hybridizable are being included. Thus, for example, while a first FNAS and SNAS species can be the gene for p53, a second FNAS and SNAS species can be a gene encoding for cytochrome c, or a nucleic acid sequence that is an enhancer element.

The "Complementary FNAS" is the sequence that is completely complementary to the FNAS.

The "Complementary SNAS" is sequence that is completely complementary to the SNAS.

The term "Homoduplex" is meant to denote the hybridized FNAS and complementary FNAS or the hybridized SNAS and the complementary SNAS. These hybridized pairs lack a mismatch.

The term "Heteroduplex" is meant to denote the set of a hybridized FNAS and a SNAS that contains a base-pair mismatch (which are not involved in the hybridization).

The term "mismatch" is meant to denote any base that, while part of a sequence that is hybridized to a second sequence, is not itself, properly Watson-Crick base-paired to a base on the second sequence. A mismatch results in a structure that is capable of being preferentially cleaved or cut by a mismatch dependent enzyme over a similar structure that does not contain the mismatch but is otherwise identical.

"Circularized heteroduplex" (CHET) denotes a heteroduplex that has been formed into a closed loop. The loop need not be made only of nucleic acids.

"Circularized homoduplex" means (CHOM) denotes a homoduplex that has been formed into a closed loop. The loop need not be made only of nucleic acids The term "Duplex" unless otherwise specified herein, refers to a circularized heteroduplex that has been cleaved. However, as will be appreciated by one of skill in the art, the "duplex" can then be circularized again, or have a section ligated in and circularized, as in the Binding Moiety Duplex.

"Binding Moiety Duplex" (BMD) denotes a duplex that has had a binding moiety associated with it. In a preferred embodiment, the BMD includes a binding moiety nucleic acid sequence, which includes the binding moiety. A BMD can include a duplex and a binding moiety, or, in some embodiments, the BMD can include a duplex and a binding moiety nucleic acid sequence (BMNAS), when the binding moiety is associated with the duplex through a nucleic acid sequence.

"Cut Binding Moiety Duplex" (CBMD), as a noun, means a BMD that has been cut so that it is no longer circular.

First and Second Adapters denote nucleic acids that can be used for further manipulation of the CBMD. In particular, the adapters can be used for amplification of the CBMD. Examples of the adapters can include poly A tails and PCR priming sites. In some embodiments, but not all, the first and second adapters are different from one another, such that two different primers (one for each adapter) are used for amplification.

The term "preferentially cutting" means that an enzyme cuts through both strands of a nucleic acid sequence in some situations but not others. An enzyme that preferentially cuts heteroduplexes, cuts a heteroduplex having two hybridized strands over a homoduplex having two hybridized strands that are, apart from the sequence forming the mismatch(es), the same. Generally, the "preferential" cutting described herein distinguishes cutting of homoduplexes from heteroduplexes. As such, the exact sequence of the strands in the duplexes is not overly important.

"Binding moiety," ("BM") is a molecule that can be used for the manipulation and/or control of anything that is associated with the binding moiety. In some embodiments this means that the binding moiety can, relatively specifically, bind to a purifying moiety under appropriate conditions. The binding moiety should be capable of being added to a duplex, for example as a binding moiety nucleic acid sequence or a polypeptide through a linker. The interaction between the binding moiety and purifying moiety is strong enough to allow enrichment and/or purification of the binding moiety and anything that is attached to it particularly the duplex. As will be appreciated by one of skill in the art, while stronger interactions can be useful and allow for more range in purification and buffer conditions, weak interactions can work as well. Biotin is an example of a binding moiety. In some embodiments, a BM is used as an insert into the duplex. In some embodiments, only a BM is covalently connected to the duplex. For example, this can occur where the binding moiety is a nucleic acid sequence that can be directly ligated into the duplex. An example of such a BM is a DNA or RNA aptamer, thereby allowing direct ligation of a BM by which the duplex can be manipulated. A nucleic acid sequence that can be bound by an antibody can also be used. In other embodiments, the binding moiety is not a nucleic acid sequence and the binding moiety is associated with the duplex without the use of a nucleic acid sequence. For example, an antibody to a sequence in the duplex can be used or any method for attaching probes to terminal nucleic acids can be used. However, in many embodiments, the section to be added to the duplex will include a nucleic acid sequence and a binding moiety already associated with the sequence. As noted above, in some embodiments the BM is capable of interacting with a purifying moiety (PM) to an extent sufficient to allow some purification and/or enrichment of the BM. However, the BM need not always require a purifying moiety. For example, a BM can be a magnetically controllable particle, allowing for the subsequent purification of the BM through the use of a magnetic field.

A "purifying moiety" is a molecule that specifically binds to the binding molecule, for example, when biotin is a binding moiety, streptavidin can be its cognate purifying moiety. In another example, digoxigenin may be a binding moiety and ant-digoxigenin antibodies may be its cognate purifying moiety.

"Enriching" means increasing the amount of one species. Relative or preferential sequence enrichment denotes that one sequence is being enriched relative to another sequence. As will be appreciated by one of skill in the art, since it is often the heteroduplex that is being amplified, both of the nucleic acid sequences in the heteroduplex can be characterized as being equally amplified (as each one is represented in the heteroduplex). However, relative to the initial sample, where, e.g., the first nucleic acid sequence was present in larger amounts than the second nucleic acid sequence, the second sequence nucleic acid sequence is being preferentially amplified or enriched. Thus, a sample that has been processed by the present invention, can contain 50% of the FNAS and 50% of the SNAS and have still undergone enrichment relative to the proportion of FNAS and SNAS in the original sample. Even lower amounts or percents of the SNAS are permissible, as long as the percent of the SNAS as a function of the combined SNAS and FNAS is greater than it was initially. Additionally, in some embodiments, the entire sequence is not being enriched, only the mismatched base and a bar code (or paired tag) on either side is enriched. However, for convenience, the process can still be characterized as relative enriching of a second nucleic acid sequence, even if it is just a part of the second nucleic acid sequence that is being enriched or detected.

"Mismatch dependent enzyme" denotes an enzyme that is capable of cleaving or cutting a nucleic acid sequence based on the presence of a base pair mismatch. Endo V is an example of a mismatch dependent enzyme. Examples of various mismatch dependent enzymes, especially variants of Endo V are disclosed in U.S. Pat. Pub. No. 2003/0148283, to Barany et al., herein incorporated by reference in its entirety. As will be appreciated by one of skill in the art, in some embodiments any form of mismatch dependent enzyme can be useful for some of the current embodiments. However, in some embodiments mismatch dependent enzymes that cleave close to the site of the mismatch are preferred. Additionally, in some embodiments, the mismatch dependent enzyme will not cleave at the mismatch but at least one or two base pairs away, although this is not required for all embodiments. In some embodiments the mismatch dependent enzyme is selected from the group consisting of Endo V, RNase A, mismatch cleavage (CCM), cleavage, CEL I, t4 endonuclease VII, MutY, mutants of any of the previous, or any combination thereof.

"Characterizing," in respect to a first or second nucleic acid sequence means providing some information regarding the nucleic acid sequence. This can include, for example, identifying the gene of which the nucleic acid sequence is a portion with which it is associated, identifying the actual sequence at the nucleic acid, identifying the location of a basepair that is involved in a basepair mismatch, and (or) identifying the actual nucleic acids involved in the basepair mismatch.

"Binding moiety nucleic acid sequence" (BMNAS) denotes a nucleic acid sequence that is associated with a binding moiety (optionally through a linker) and ligated into the duplex. In some embodiments, the BMNAS can contain degenerate ends. Effectively, this means that multiple BMNASs are used, each having different nucleic acid sequences on the ends. This can allow for better insertion of the BMNAS into a duplex that has sticky ends. In some embodiments, the BMNAS contains restriction sites. In some embodiments, these restriction sites allow for cleavage 20 to 30 base pairs away from the site.

"Bar code sequence," "identifying code sequence," and "paired tag," denote a nucleic acid sequence that is sufficient to allow for the identification of a gene or sequence of interest. The bar code sequence can be, but need not be, a small section of the original nucleic acid sequence on which the identification is to be based. For example, in situations in which an entire genome is already known, then the bar code need only be long enough to allow one to identify where the nucleic acid sequences belong in the genome, thereby allowing one to identify the gene or sequence of interest using a very short identifying sequence. In some embodiments the bar code is 15-30 nucleic acids long.

"Gene" or "sequence of interest" denotes the gene or sequence that one is interested in identifying or characterizing.

"Nucleobase" means any nitrogen-containing heterocyclic moiety capable of forming Watson-Crick hydrogen bonds in pairing with a complementary nucleobase, including nucleobase analogs, e.g. a purine, a 7-deazapurine, or a pyrimidine. Typical nucleobases are the naturally occurring nucleobases adenine, guanine, cytosine, uracil, thymine, and analogs of the naturally occurring nucleobases (Seela, U.S. Pat. No. 5,446,139), e.g. 7-deazaadenine, 7-deazaguanine, 7-deaza-8-azaguanine, 7-deaza-8-azaadenine, inosine, nebularine, nitropyrrole (Bergstrom, J. Amer. Chem. Soc. 117:1201-09 (1995)), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, $O^6$-methylguanine, $N^6$-methyladenine, O⁴-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman, in Practical Handbook of Biochemistry and Molecular Biology, pp. 385-394, CRC Press, Boca Raton, Fla. (1989)). The term "nucleobase" includes those naturally occurring and those non-naturally occurring heterocyclic moieties commonly known to those who utilize nucleic acid technology or utilize peptide nucleic acid technology to generate polymers which can sequence-specifically bind to nucleic acids.

"Nucleoside" refers to a compound comprising a nucleobase linked to the C-1' carbon of a sugar, such as ribose, arabinose, xylose, and pyranose, in the natural beta or the alpha anomeric configuration. The sugar can be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_{12}$ alkyl, or $C_3$-$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g. 2'-O-methyl, 4'-alpha-anomeric nucleotides, 1'-alpha-anomeric nucleotides (Asseline Nucl. Acids Res. 19:4067-74 (1991)), 2'-4'- and 3'-4'-linked and other "locked" or "LNA", bicyclic sugar modifications (WO 98/22489; WO 98/39352; WO 99/14226). Exemplary LNA sugar analogs within a polynucleotide include the structures on page 4 of U.S. Patent Publication 2003/0198980, to Greenfield et al., on Oct. 23, 2003, where B is any nucleobase.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi Nucl. Acids Res. 21:4159-65 (1993); Fujimori, J. Amer. Chem. Soc. 112:7435 (1990); Urata, Nucleic Acids Symposium Ser. No. 29:69-70 (1993)). When the nucleobase is purine, e.g. A or G, the ribose sugar is usually attached to the N⁹-position of the nucleobase. When the nucleobase is pyrimidine, e.g. C, T or U, the pentose sugar is usually attached to the N¹-position of the nucleobase (Kornberg and Baker, DNA Replication, 2$^{nd}$ Ed., Freeman, San Francisco, Calif. (1992)).

"Nucleotide" refers to a phosphate ester of a nucleoside, as a monomer unit or within a nucleic acid. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. alpha.-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "nucleic acid" refers to natural nucleic acids, artificial nucleic acids, analogs thereof, or combinations thereof.

As used herein, the terms "polynucleotide" and "oligonucleotide" are used interchangeably and mean single-stranded and double-stranded polymers of nucleotide monomers (nucleic acids), including, but not limited to, 2'-deoxyribonucleotides (DNA) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as H⁺, NH$_4^+$, trialkylammonium, Mg$^{2+}$, Na⁺ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

As used herein, the term "nucleic acid sequence" or "nucleobase sequence" is any section of a polymer which comprises nucleobase-containing subunits Non-limiting examples of suitable polymers or polymer segments include oligonucleotides, oligoribonucleotides, peptide nucleic acids and analogs and chimeras thereof.

An "analog" nucleic acid is a nucleic acid that is not normally found in a host to which it is being added or in a sample that is being tested. For example, the target sequence will not comprise an analog nucleic acid. This includes an artificial, synthetic, or combination thereof, nucleic acid. Thus, for example, in one embodiment, PNA is an analog nucleic acid, as is L-DNA and LNA (locked nucleic acids), iso-C/iso-G, L-RNA, O-methyl RNA, or other such nucleic acids. In one embodiment, any modified nucleic acid will be encompassed within the term analog nucleic acid. In another embodiment an analog nucleic acid can be a nucleic acid that will not substantially hybridize to native nucleic acids in a system, but will hybridize to other analog nucleic acids; thus, PNA would not be an analog nucleic acid, but L-DNA would be an analog nucleic acid. For example, while L-DNA can hybridize to PNA in an effective manner, L-DNA will not hybridize to D-DNA or D-RNA in a similar effective manner. Thus, nucleotides that can hybridize to a probe or target sequence but lack at least one natural nucleotide characteristic, such as susceptibility to degradation by nucleases or binding to D-DNA or D-RNA, are analog nucleotides in some embodiments. Of course, the analog nucleotide need not have every difference.

"Enzymatically extendable" refers to a nucleotide which is: (i) capable of being enzymatically incorporated onto a terminus of a polynucleotide through the action of a polymerase enzyme, and (ii) capable of supporting further primer extension. Enzymatically extendable nucleotides include nucleotide 5'-triphosphates, i.e. dNTP and NTP, and labelled forms thereof.

"Enzymatically incorporatable" refers to a nucleotide which is capable of being enzymatically incorporated onto a terminus of a polynucleotide through the action of a polymerase enzyme. Enzymatically incorporatable nucleotides include dNTP, NTP, and 2',3'-dideoxynucleotide 5'-triphosphates, i.e. ddNTP, and labelled forms thereof.

"Terminator nucleotide" means a nucleotide which is capable of being enzymatically incorporated onto a terminus of a polynucleotide through the action of a polymerase enzyme, but cannot be further extended, i.e. a terminator nucleotide is enzymatically incorporatable, but not enzymatically extendable. Examples of terminator nucleotides include ddNTP and 2'-deoxy, 3'-fluoro nucleotide 5'-triphosphates, and labelled forms thereof.

"Primer" means an oligonucleotide of defined sequence that is designed to hybridize with a complementary, primer-specific portion of nucleic acid sequence, and undergo primer extension. A primer functions as the starting point for the polymerization of nucleotides (Concise Dictionary of Biomedicine and Molecular Biology, CPL Scientific Publishing Services, CRC Press, Newbury, UK (1996)).

The term "primer extension" means the process of elongating a primer that is annealed to a target in the 5' to 3' direction using a template-dependent polymerase. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand.

Figure 2:
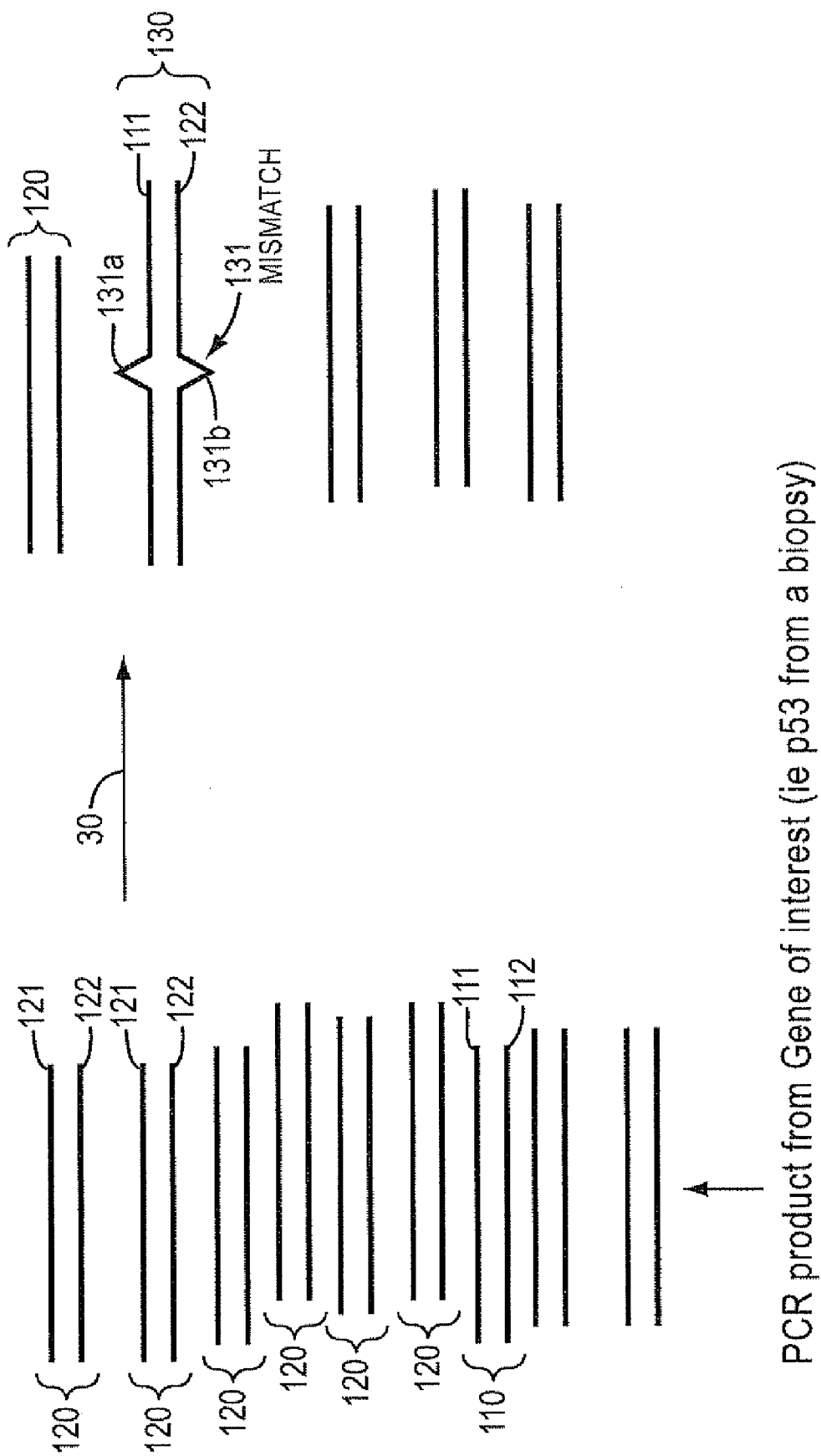
FIG. 2 depicts an initial step of forming a heteroduplex and a homoduplex nucleic acid sequence.
Figure 3:
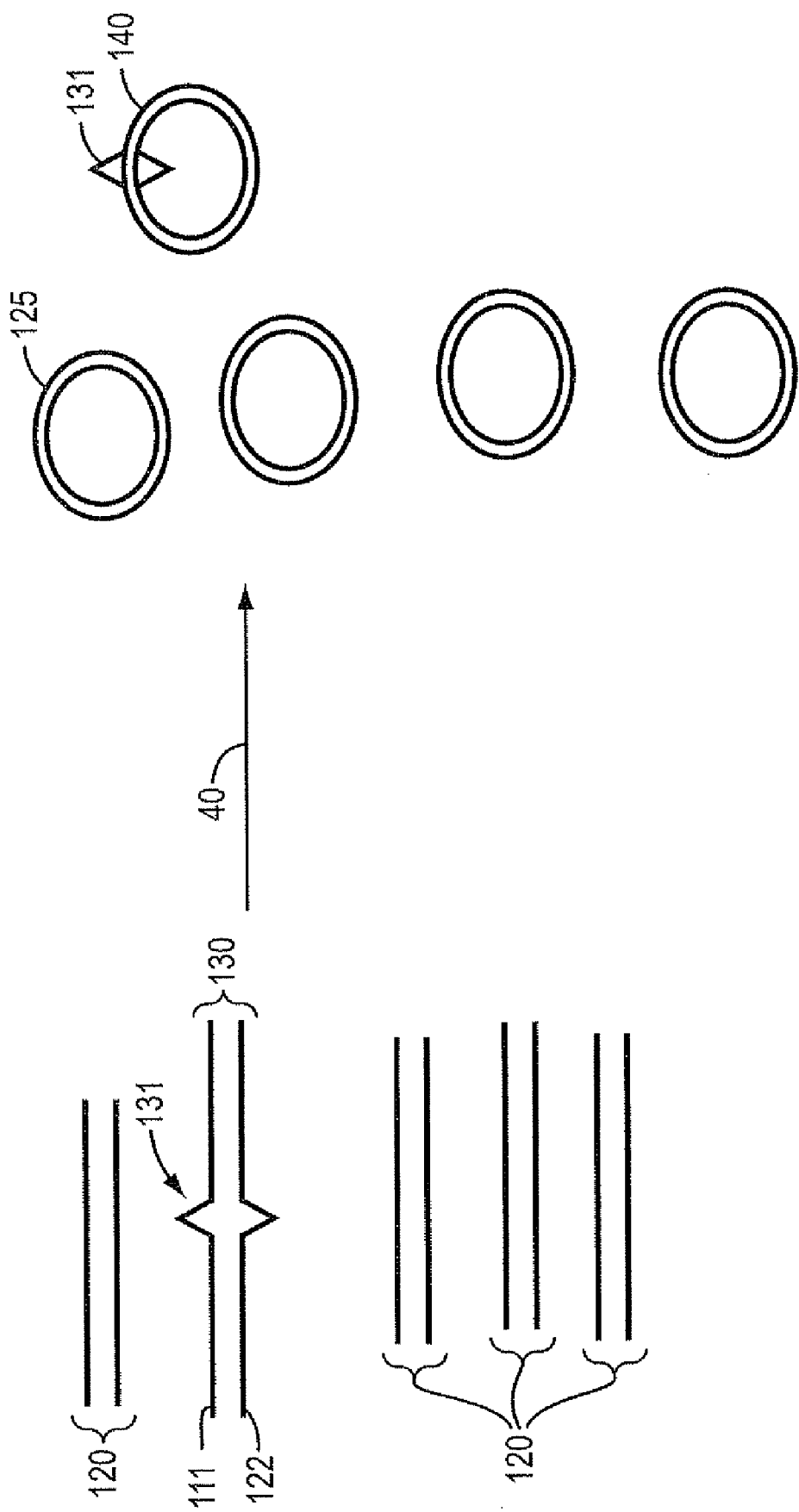
FIG. 3 depicts a step of circularizing the homoduplex and heteroduplex nucleic acid sequences.
Figure 10:
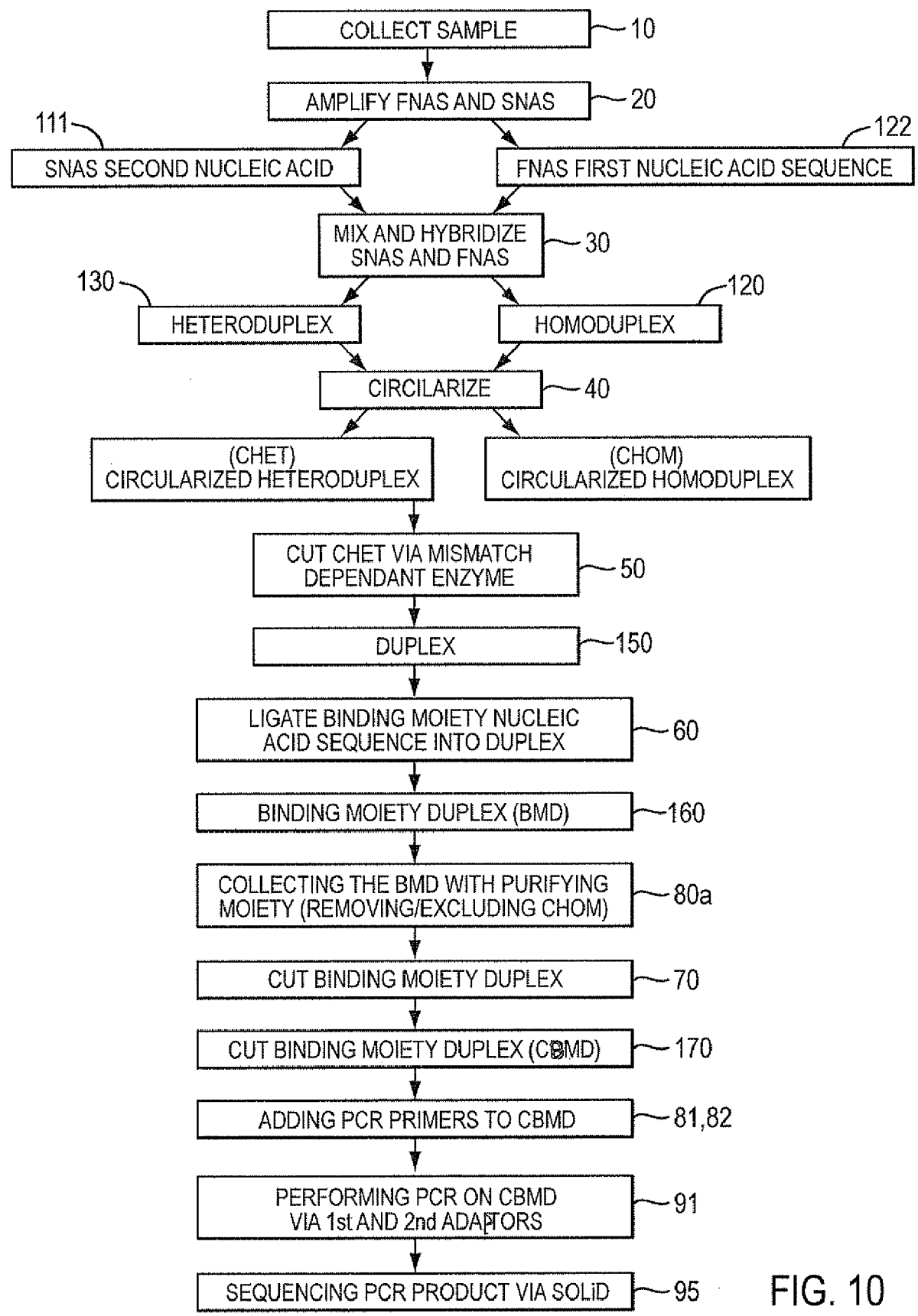
FIG. 10 is a flow chart depicting an embodiment in which a section of a second nucleic acid sequence is enriched relative to an amount of a section of a first nucleic acid sequence.

"Target," "target polynucleotide," "target sequence," or similar term means a specific polynucleotide sequence, the presence or absence of which is to be determined, or which is to be enriched in a sample. In some embodiments the target is the SNAS. The sequence is subject to hybridization with a complementary, or in certain steps or embodiments, a nearly complementary polynucleotide, e.g. to form a heteroduplex. In some embodiments, the target sequence will be one of (or part of) the second nucleic acid sequences. As depicted in FIG. 2 and FIG. 10, the target nucleic acid sequence is at least part of the second nucleic acid sequence. In some embodiments, the target sequence is the sequence that is to be enriched in subsequent steps. In some embodiments, the target sequence can also be described as the "minority sequence." For example, in FIG. 2, the sequences 111 and 112 are less abundant than and are to be enriched relative to the 121 and 122 sequences. In this embodiment, the target sequences would also be minority sequences.

The "target sequence" can comprise the entire polymer or can be a sub-sequence of the sequence of interest. The target sequence can include any nature of nucleotide as well, for example, PNA, cDNA, mRNA, antisense RNA, siRNA, or microRNA (for a discussion of miRNA see Grishok et al., Cell, 106:2334 (2001); Carrington and Ambros, Science 301: 336-338 (2003)). This can also apply to the FNAS and SNAS.

The term "control sequence" describes a sequence over which the target sequence is to be enriched. The control sequence will hybridize (although it will form a heteroduplex) with the target sequence. In some embodiments, the control sequence is the sequence that is present in large amounts relative to the target sequence. For example, in FIG. 2, the control sequences would be the first nucleic acid sequences 122 and 121. Where appropriate, this sequence can be known as the "majority sequence." For example, in FIG. 2, sequences 121 and 122 are not only the control sequence, but are also the majority sequences, over which the minority sequence (at least one of) 111 and 112 is to be enriched. However, as described herein, the term "majority sequence" need not apply to all embodiments of control sequences or FNASs, that is, there can be embodiments in which the control sequence or FNAS are not the majority sequences in a sample. Regardless, the "control sequence" forms a heteroduplex with the target sequence. As will be appreciated by one of skill in the art, enrichment does not require an end result in which there is more target sequence than control sequence, but merely that there is a greater amount of target sequence (compared to the amount of control sequence) than previously present in the sample. In some embodiments, only the target sequence will be present following the enrichment. As will be appreciated by one of skill in the art, the control sequence can be obtained in any manner. For example, it can be part of the original sample. In alternative embodiments, the control sequence is added to a sample to determine if a particular target sequence is present in the sample. Thus, there are embodiments in which enrichment of a target sequence can occur, even if there is no control sequence present with the target sequence initially. However, as will be appreciated by one of skill in the art, the terms control and target sequence can still be used, as the target sequence will be increased relative to the amount of control sequence present (although this amount is initially none).

The FNAS and/or SNAS can be composed of DNA, RNA, analogs thereof, or combinations thereof. The FNAS and/or SNAS can be single-stranded or double-stranded. A FNAS and/or SNAS can be derived from any living, or once living, organism, including but not limited to prokaryote, eukaryote, plant, animal, and virus. The FNAS and/or SNAS can originate from a nucleus of a cell, e.g., genomic DNA, or can be extranuclear nucleic acid, e.g., plasmid, mitochondrial nucleic acid, various RNAs, and the like. The FNAS and/or SNAS can be first reverse-transcribed into cDNA if the target nucleic acid is RNA, if so desired. A variety of methods are available for obtaining a FNAS and/or SNAS for use with the compositions and methods described herein. When the FNAS and/or SNAS is obtained through isolation from a biological sample, possible isolation techniques include (1) organic extraction followed by ethanol precipitation, e.g., using a phenol/chloroform organic reagent (e.g., Ausubel et al., eds., Current Protocols in Molecular Biology Volume 1, Chapter 2, Section I, John Wiley & Sons, New York (1993)), or an automated DNA extractor (e.g., Model 341 DNA Extractor, Applied Biosystems, Foster City, Calif.); (2) stationary phase adsorption methods (e.g., Boom et al., U.S. Pat. No. 5,234, 809; Walsh et al., Biotechniques 10(4); 506-513 (1991)), and (3) salt-induced DNA precipitation methods (e.g., Miller et al., Nucleic Acids Research, 16(3): 9-10 (1988)). In one embodiment, the FNAS and/or SNAS can be mRNA. As noted herein, the FNAS and SNAS do not have to be obtained or synthesized, as they can be present in a sample.

The terms "annealing" and "hybridizing" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "solid support" refers to any solid phase material upon which an oligonucleotide is synthesized, attached or immobilized. Solid support encompasses terms such as "resin", "solid phase", and "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as, for example, glass, silica, controlled-pore-glass (CPG), or reverse-phase silica. The configuration of a solid support can be in the form of beads, spheres, particles, granules, a gel, a surface, or combinations thereof. Surfaces can be planar, substantially planar, or non-planar. Solid supports can be porous or non-porous, and can have swelling or non-swelling characteristics. A solid support can be configured in the form of a well, depression or other container, vessel, feature or location or position. A plurality of solid supports can be configured in an array at various locations, e.g., positions, addressable for robotic delivery of reagents, or by detection means including scanning by laser illumination and confocal or deflective light gathering.

"Array" or "rmicroarray" encompasses an arrangement of polynucleotides present on a solid support or in an arrangement of vessels. Certain array formats are referred to as a "chip" or "biochip" (M. Schena, Ed. Microarray Biochip Technology, BioTechnique Books, Eaton Publishing, Natick, Mass. (2000)). An array can comprise a low-density number of addressable locations, e.g. 1 to about 12, medium-density, e.g. about a hundred or more locations, or a high-density number, e.g. a thousand or more. Typically, the array format is a geometrically-regular shape which allows for fabrication, handling, placement, stacking, reagent introduction, detection, and storage. The array can be configured in a row and column format, with regular spacing between each location. Alternatively, the locations can be bundled, mixed, or homogeneously blended for equalized treatment and/or sampling. An array can comprise a plurality of addressable locations configured so that each location is spatially addressable for high-throughput handling, robotic delivery, masking, and/or sampling of reagents and/or by detection means including scanning by laser illumination and confocal and/or deflective light gathering. The array may comprise one or more "addressable locations," e.g., "addressable positions," that is, physical locations that comprise a known type of molecule.

A "suspension array" is one alternative composition or method for performing analyte detection and/or quantification. In a suspension array, the solid phase consists of particles in solution. Each particle member of the array has a characteristic, such as a shape, pattern, chromophore or fluorophore that uniquely identifies the particle, e.g., bead.

Mismatch Dependent Nucleic Acid Enrichment

The identification of relatively rare mutations in nucleic acid sequences, especially when a sample contains other similar or nearly identical nucleic acid sequences, can be technically challenging, especially when the nucleic acid sequence of interest is a minority of the total population of nucleic acid sequences. Simply using PCR amplification may not result in a meaningful amplification of the desired nucleic acid sequence, as the primers used for PCR amplification will likely be just as effective on both species.

As outlined above, the present technique uses the presence of a mismatch in a heteroduplex in order to selectively enrich a particular nucleic acid sequence for further processing. In some embodiments, this means amplifying the minority nucleic acid sequence so that it can be sequenced.

In some embodiments, a nucleic acid sequence is amplified that, while present in a sample, is masked by the presence of a large number of other similar (or nearly identical) nucleic acid sequences). In some embodiments, the first step for this process is shown in FIG. 2 in which a first nucleic acid sequence duplex 120 comprising a first nucleic acid sequence 122 and a complementary first nucleic acid sequence 121 are paired in a homoduplex. As shown in the figure, the sample contains a relatively large amount of the homoduplexes 120. In addition to these homoduplexes 120, the solution can contain a relatively small amount of a homoduplex 110, which can contain a mutant nucleic acid sequence (or, more generally, a second nucleic acid sequence). The homoduplex of the second nucleic acid sequence 110 includes a second nucleic acid sequence 111 hybridized to a complementary second nucleic acid sequence 112. In many embodiments, this can be the starting arrangement for the sample. As noted below, if sequences are known, the presence of these two nucleic acid homoduplexes can be increased by PCR, thereby reducing the relevance of other nucleic acid sequences in a sample; however, this step is not necessary in all embodiments, for example if target is not known.

In order to create the initial heteroduplex, by which further selection will be controlled, one can melt the various homoduplexes 120 and 110 to separate the homoduplexes. One then allows the duplexes to reanneal to form a heteroduplex 130. This is shown in FIG. 2 as step 30. The reannealing results in the reformation of a large number of homoduplexes 120 of the FNASs and the formation of a heteroduplex 130, which includes the second nucleic acid sequence 111 (or its complement 112) and a first nucleic acid sequence 122 (or its complement 121). The heteroduplex 130 contains at least one mismatch 131. In embodiments in which there is a traditional mismatch (instead of simply a deletion or insertion in one sequence) there is at least one base pair in each of the nucleic acid sequences 111 and 122 that does not match. These are identified as 131a and 131b in FIG. 2. However, as will be appreciated by one of skill in the art, there is no need for a base pair to be part of the mismatch in each strand, as there can be insertions or deletions that lead to the formation of the mismatch. Similarly, there is no limit on the number of bases that are part of the mismatch in each strand. In some embodiments it is a single base in each strand, in other embodiments, 1-3, 3-5, 5-10, 10-15, 15-30, 30-50, or more bases are involved in the mismatch.

As shown in FIG. 2, after melting and reannealing the sample can be a mixture of homoduplexes 120 and heteroduplexes 130. At this point, the heteroduplexes are typically a relative minority compared to the population of homoduplexes.

Once the heteroduplex 130 is formed, the heteroduplexes 130 and the homoduplexes 120 are circularized 40 to form a circularized heteroduplex (CHET) 140 and a circularized homoduplex (CHOM) 125.

Figure 4:
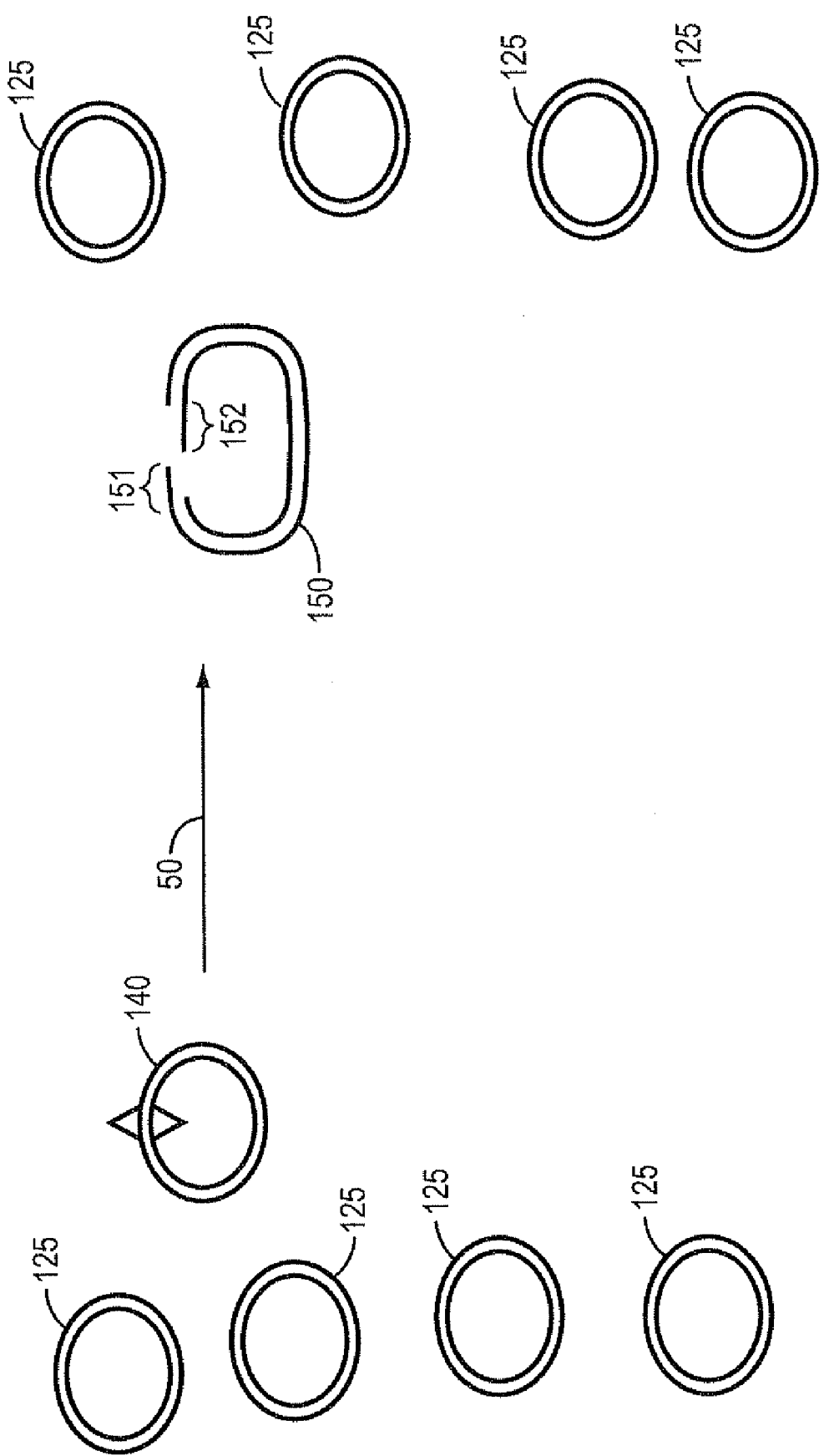
FIG. 4 depicts a step of mismatch dependent cutting of the heteroduplex while the circularized homoduplex molecule remains relatively whole.

Following this step, the sample containing the circularized homoduplex 125 and heteroduplex 140 molecules is treated with an enzyme that recognizes and cleaves based on the presence of a mismatch, as shown in FIG. 4, step 50. Because only the circularized heteroduplexes (CHETs) 140 will have the mismatch, only these CHETs will be cleaved to form a duplex 150. The circularized homoduplexes 125 will stay closed. If the duplex 150 includes sticky ends 151 and 152, these can be blunted if desired.

Figure 5:
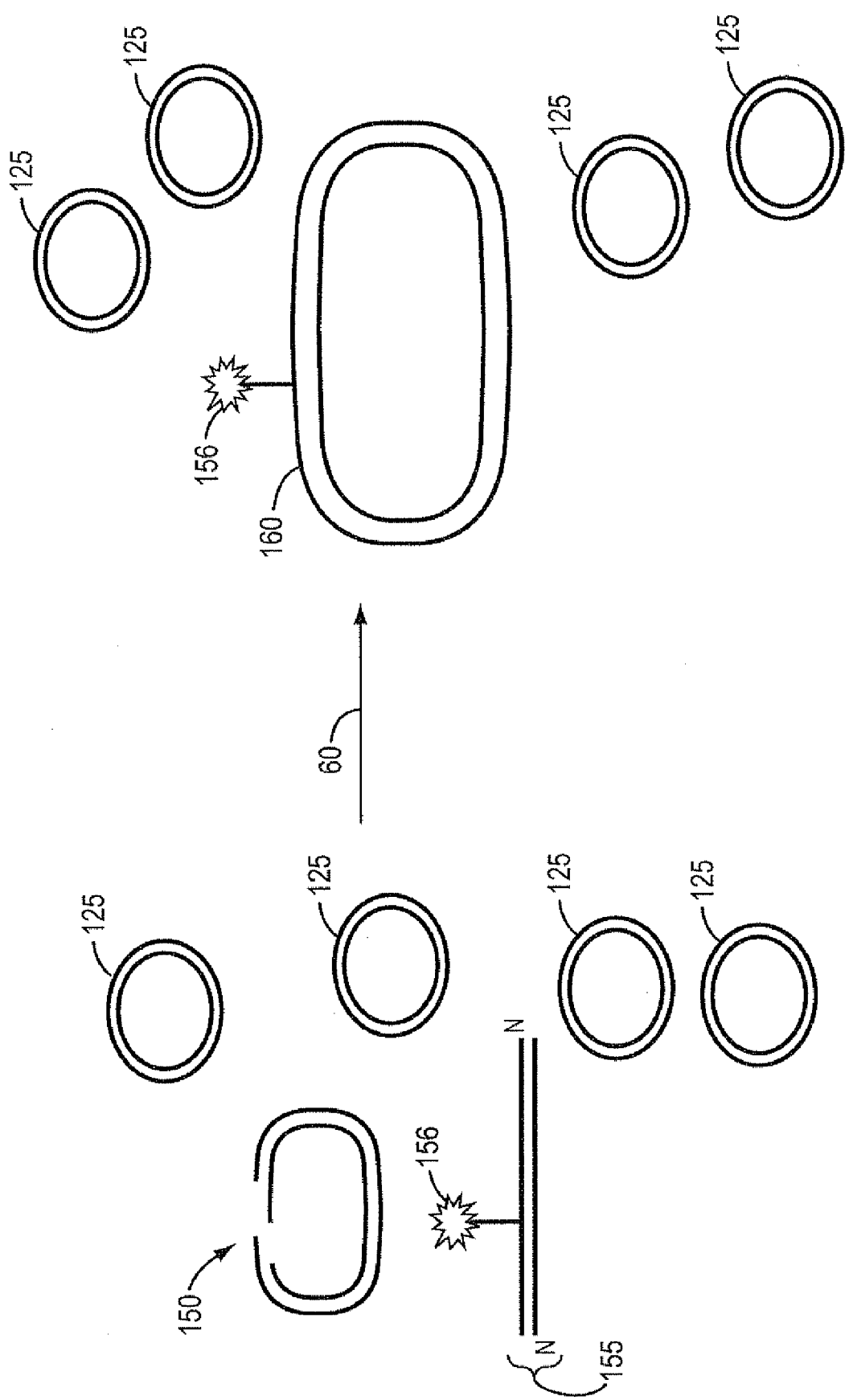
FIG. 5 depicts a step of inserting one embodiment of a binding moiety nucleic acid sequence into a duplex to form the binding moiety duplex.

Following the formation of the duplex 150, a binding moiety nucleic acid sequence (BMNAS) 155 is ligated into the duplex 150 to form a binding moiety duplex 160, as show in FIG. 5. The binding moiety nucleic acid sequence 155 can include a nucleic acid sequence to allow its ready ligation into the duplex 150. The binding moiety nucleic acid sequence 155 can include degenerate ends 153a and 153b (FIG. 6) allowing for the possible variability of mismatch dependent cutting which results in the sticky ends 151 and 152 of the duplex 150.

Figure 9:
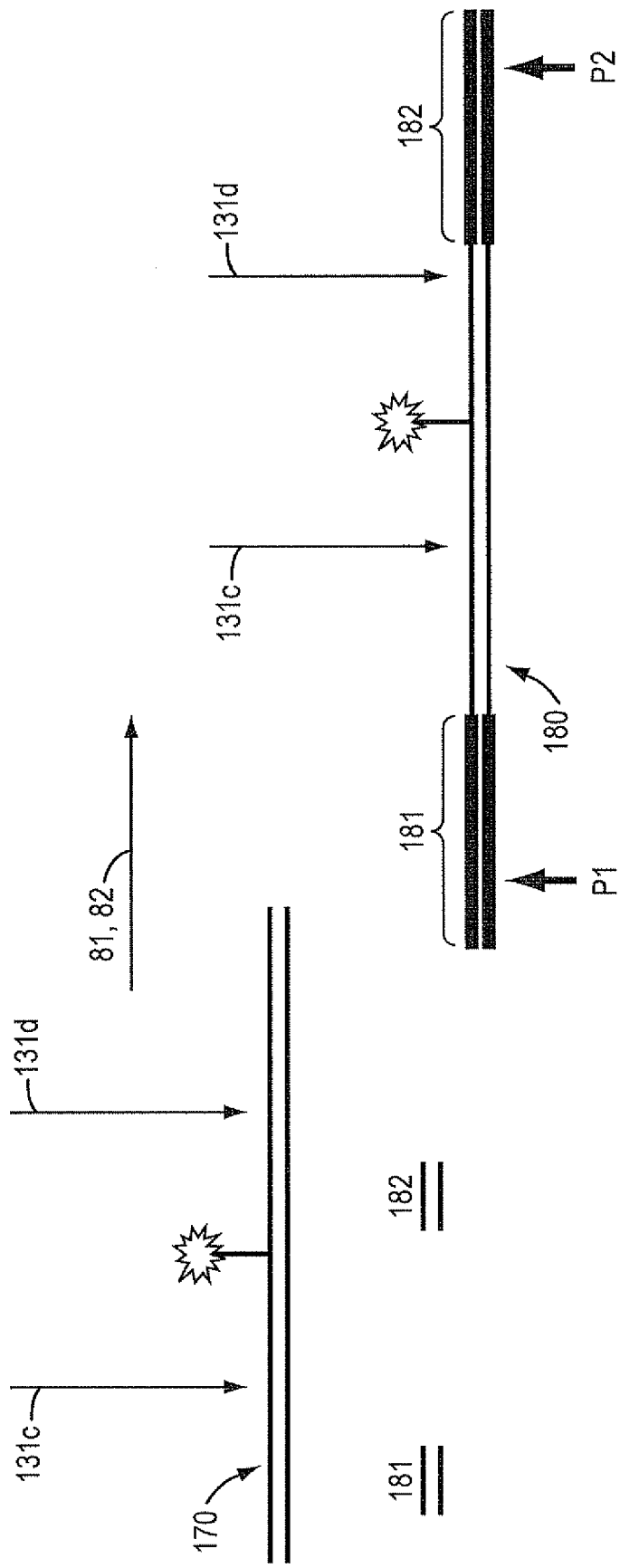
FIG. 9 depicts a step of adding two different adapters, P1 and P2, to the cut binding moiety duplex.

Because the CHOMs 125 have not been cut, since they lack an effective restriction site (i.e., mismatch), the binding moiety nucleic acid sequence will not be ligated into those nucleic acid sequences in step 60 (FIG. 5). Thus, at this point, the solution will contain the binding moiety duplex 160 which includes the binding moiety nucleic acid sequence 155 and the duplex 150 and the solution will further include the initial CHOMs 125. As will be appreciated by one of skill in the art, while a binding moiety nucleic acid sequence can be used, any method or composition that allows for the selective addition of a binding moiety to the duplex 150, without a significant amount of addition of the BM to the CHOMs 125 can be used as well. Thus, in some embodiments, the BM is associated with the duplex without a nucleic acid sequence insert (BMNAS). For example, the linearized sequences (duplex 150) can be separated from the circularized CHOMs 125 and then a BSM can be added to any of the linear strands (duplexes 150). Of course, in such an embodiment, the need for a BM is greatly reduced and the duplex can have adapters added to it directly, as shown in FIG. 9, without the need for the BM, as the product has already been separated from the excessive population of CHOMs.

Figure 6:
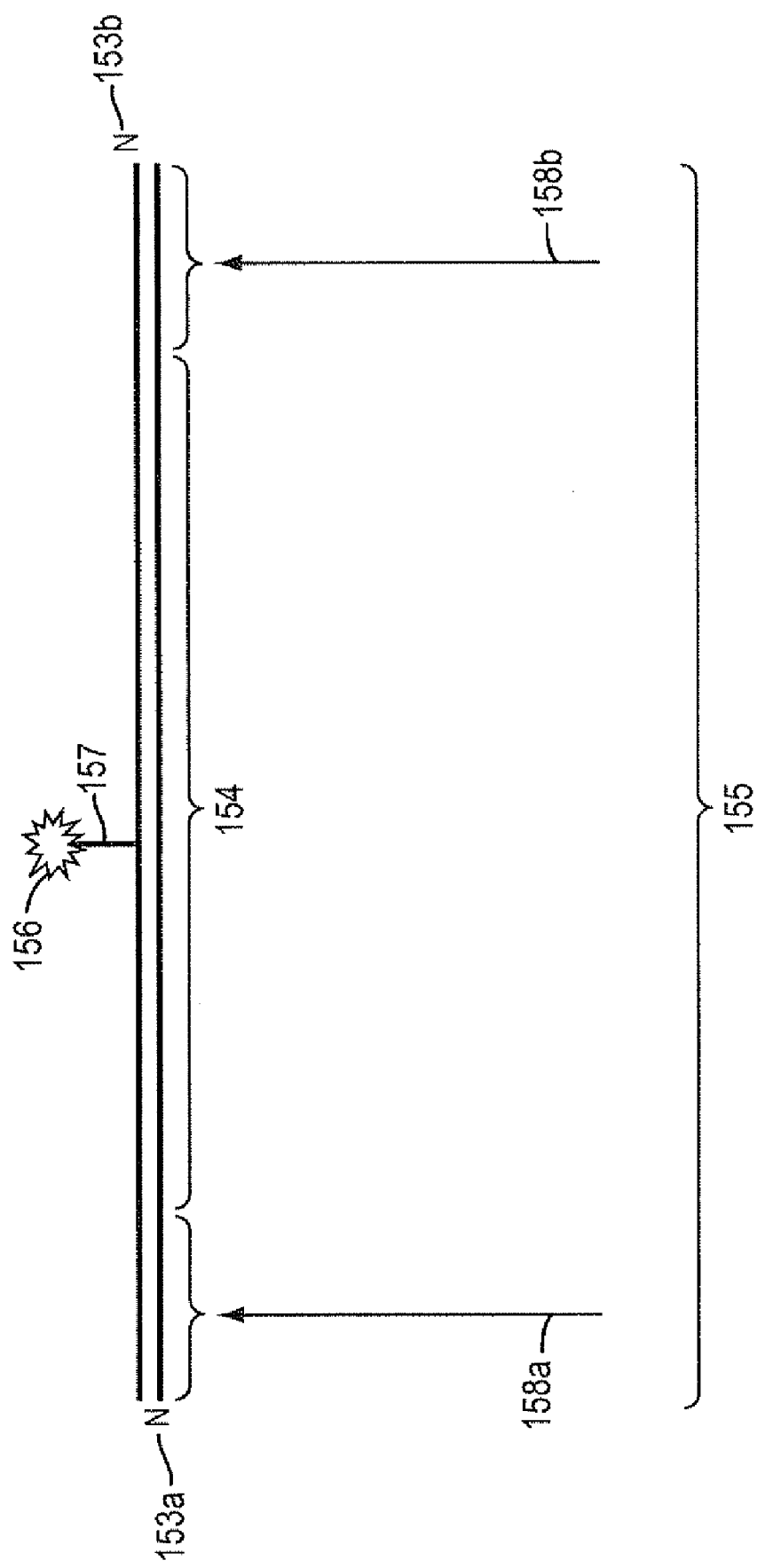
FIG. 6 depicts the various parts of various embodiments of a binding moiety nucleic acid sequence.

One embodiment of the BMNAS 155 used is that depicted in FIG. 6. The BMNAS 155 can include a nucleic acid sequence 154 that is associated to a binding moiety 156 optionally through a linker 157. In some embodiments, the binding moiety nucleic acid sequence 155 includes restriction sites 158a and 158b on one or both sides of the binding moiety nucleic acid sequence. In some embodiments, the restriction sites 158a and 158b are EcoP15I sites. As will be appreciated by one of skill in the art, any number of possible restriction cites can be used. In embodiments in which a bar code is to be used to identify the location or identity of the nucleic acid sequence, then a restriction enzyme that cleaves distally to the sites 158a and 158b is preferred, allowing for the cleaved product 170 (FIG. 7) to retain the bar code sections 171a and 171b. As will be appreciated by one of skill in the art, in embodiments in which a bar code is not required (e.g., when the identity of the nucleic acid sequence is known), the restriction sites can cleave at the restriction sites themselves.

In some embodiments, the binding moiety nucleic acid sequence 155 can include degenerate ends 153a and/or 153b. In such embodiments, the ends are degenerate to allow the effective ligation of the BMNAS 155 into a variety of the possible duplexes 150, without requiring that one actually know what the overhang 151 and 152 in the duplex 150 will be. In such embodiments, each end of the BMNAS 155 includes at least one additional nucleic acid to allow for at least one BMAS 155 to effectively anneal into any and all possible duplexes 150 resulting from the cutting of the CHET 140. In effect, this means that the ends of the BMNAS 155 are degenerate across the population of BMNASs. As will be appreciated by one of skill in the art, the degenerate ends 153a and 153b can be any number of nucleic acids. In some embodiments, the degenerate ends are one nucleic acid on each end therefore allowing for 16 different BMNASs to form an entire library of all possible arrangements of nucleic acids at each end of the BMNAS. By using this combination of BMNASs, any possible cleavage site resulting from the cleavage of the duplex 150 can effectively be ligated to at least one BMNAS (assuming that there is a single nucleotide overhang 151 and 152 on each side).

As will be appreciated by one of skill in the art, in some embodiments the overhangs produced in the cutting of the CHET to form the duplex 150 can be more than one nucleic acid in length; for example, two nucleic acids long. As will be appreciated by one of skill in the art, the longer the overhang the more variability there is in the overhangs, and thus the larger the number of possible BMNAS required to ensure that one will readily anneal to the duplex 150. Thus, a larger number of BMNASs can be employed to make certain that effective ligation is achieved between the BMNAS and the duplex. For example, 256 variations of a BMNAS (with the variation being 2 nucleic acids at each end) can be used when there are two nucleic acids of overhang 151 and 152. The number of degenerate ends can be larger as well.

As will be appreciated by one of skill in the art, the binding moiety 156 can be any moiety that allows for the association of the binding moiety nucleic acid sequence with a purifying moiety. In some embodiments, the binding moiety is biotin. In some embodiments, the linker 157 allows biotin to be covalently linked to a nucleic acid 154.

Following the creation of the binding moiety duplex BMD 160 (FIG. 5), the binding moiety duplex can be purified through the use of a binding moiety. However, in many embodiments, the binding moiety duplex is first further processed by cutting at the restriction sites that are in the BMD 160, as part of the BMNAS 155.

Figure 7:
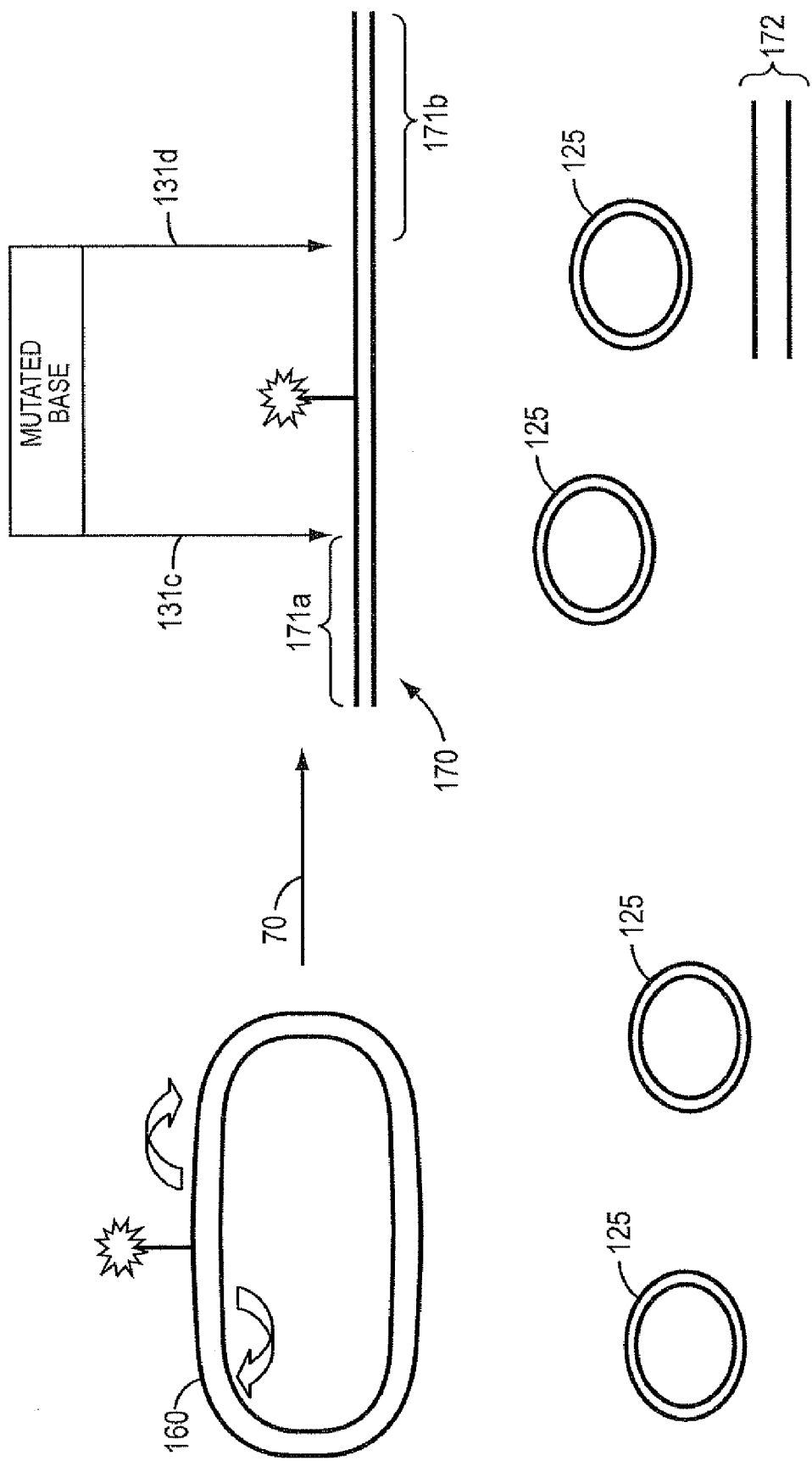
FIG. 7 depicts a step of cutting the binding moiety duplex (BMD) to form the cut binding moiety duplex (CBMD).

This cutting of the BMD 160 in step 70 results in the creation of a cut binding moiety duplex CBMD 170, shown in FIG. 7. In embodiments in which the binding moiety nucleic acid sequence 155 includes two such restriction sites (158a and 158b), cutting the BMNAS 160 can result in a double-cut binding moiety duplex CBMD (170) and an excised section 172 that contains the remainder of the first and second nucleic acid sequences. While a large portion of the first and second nucleic acid sequences can be removed in this step, the cut binding moiety duplex 170 can still include the binding moiety nucleic acid sequence, the nucleic acids involved in the basepair mismatch (e.g., in some examples a point mutation), and bar code sections 171a and 171b on either side of the binding moiety nucleic acid sequence.

Figure 8:
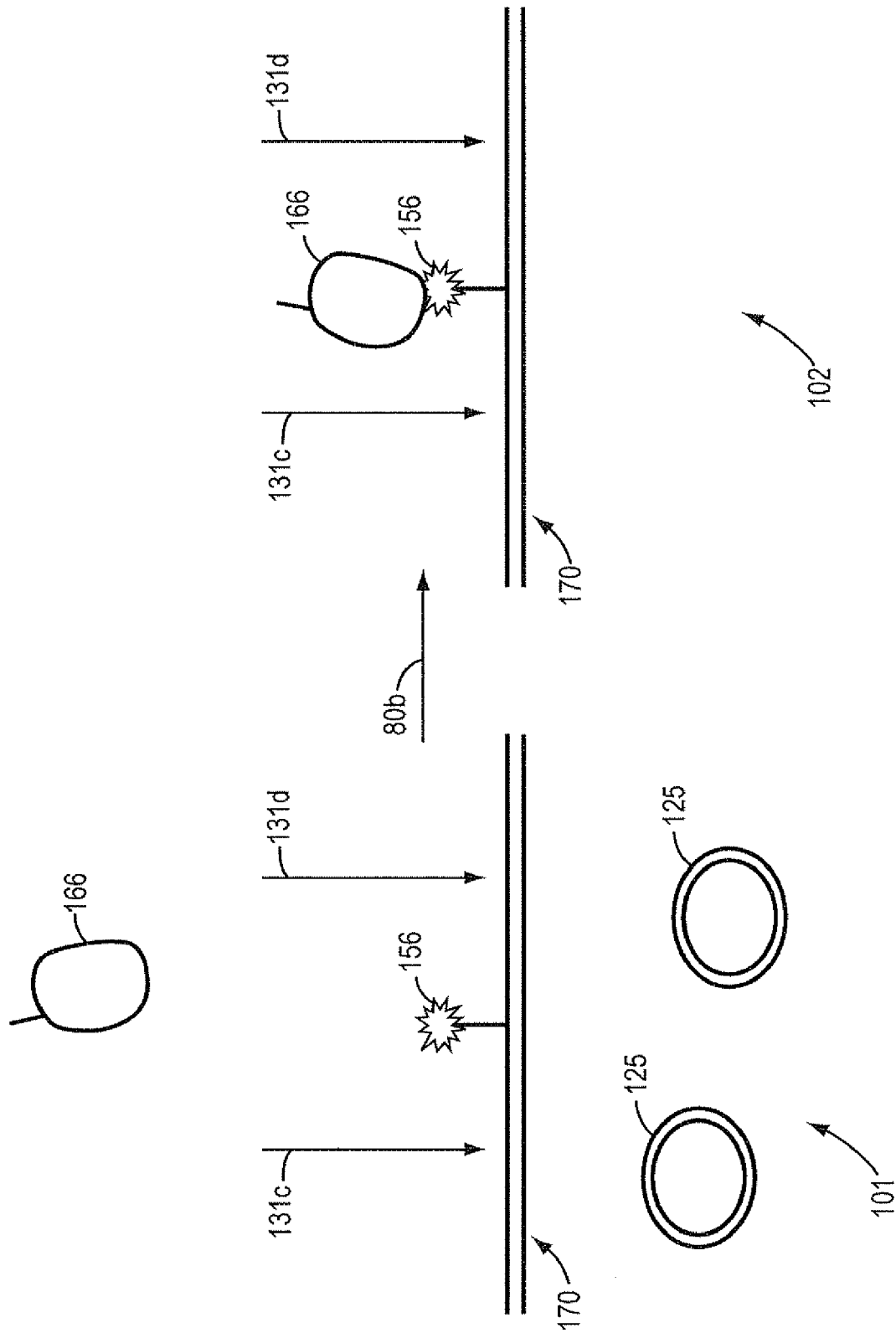
FIG. 8 depicts a step of selecting the binding moiety, thereby enriching a sample for the base pair involved in the mismatch.

At this point, depending on whether or not the purification step has already been performed, the solution may or may not contain circularized homoduplexes 125 as well as the cut binding moiety duplex (CBMD) 170. In situations in which purification has yet to occur, the cut binding moiety duplex 170 can then be purified away from the CHOMs 125 through the use of an appropriate purifying moiety that will combine to the binding moiety 156. This is shown in FIG. 8 in step 80b in which solution 101, containing both the cut binding moiety duplex 170 and the CHOM 125, undergo purification to result in the solution 102 containing effectively the cut binding moiety duplex 170 without the homoduplexes 125 and optionally without the excess first and second nucleic acid sections 172. As will be appreciated by one of skill in the art, this results in an enrichment of the molecules involved in the heteroduplex (both 111 and 122) over the original composition that contained primarily the homoduplexes 120. In some embodiments, this can result in approximately 50% of the sample being at least one of 111 or 112 (with the other half being either 121 or 122).

In some embodiments, further processing occurs to prepare the cut binding moiety duplex (CBMD) 170 for additional amplification and subsequent characterization, such as sequencing or identification. One such embodiment is shown in FIG. 9. The cut binding moiety duplex (CBMD) 170 has adapters 181 and 182 attached to it in steps 82 and 82, which, in some embodiments are primer sites (or "primer binding sites"). The attachment of the adapters 181 and 182 to the CBMD 170 results in an adapter containing CBMD 180. In some embodiments, the two primer binding sites 181 and 182 are on either side of the CBMD 170. The adapters can be used for amplification of the adapter containing CBMD 180, and especially the bases responsible for the mismatch, located at position 131c and 131d. In some embodiments, amplification is performed by emulsion PCR. In some embodiments, the adapters 181 and 182 are different from one another.

The amplified product can then be sequenced. For example, in some embodiments a highly parallel non-electrophoretic sequencing technique is used. As will be appreciated by one of skill in the art, due to the presence of the bar codes and the shortened length of the first and second nucleic acid sequences, sequencing techniques that work optimally on relatively short lengths of nucleic acids (for example less than 100, 100-60, 60-40, 40-30, 30-20, 20-10, 10-5, or fewer nucleic acids) can be useful for sequencing many of these products 180, as the lengths can be ideal for such techniques, while supplying an adequate sequence of the section in question (e.g., the bar codes and/or the sequence at the mismatch).

As will be appreciated by one of skill in the art, various embodiments of the above methods and compositions can have various utilities at the various stages. For example, as soon as the BM 156 is associated with the duplex 150, one can concentrate or enrich a sample for a heteroduplex. Alternatively, while determining the sequence of the second nucleic acid at the site of the mismatch 131 can reveal the exact nature of the difference(s) between the first and second nucleic acid sequences, it need not be performed in all methods, as simply knowing that there is a variant (e.g., mutant) sequence present in a certain gene or sequence or at a certain location in a gene or sequence can be useful for many purposes. As such, not every step need be performed in every method. However, the following section outlines one possible embodiment of an enrichment and characterization of the nucleic acid sequence.

In some embodiments, the above technique is used to not merely enrich for a particular nucleic acid sequence, but determine if a sequence is present in a biological sample. Such an embodiment is displayed in FIG. 10. In such an embodiment, an initial step a sample is collected, as shown in step 10. A first nucleic acid sequence and a second nucleic acid sequence are then amplified (one of which can be, for example, a wildtype gene sequence from healthy cells in the sample and the other a mutant gene sequence from cancerous cells in the sample) by PCR in step 20. In some embodiments the first and second nucleic acid sequences (as well as their complementary sequences) are PCR amplified using the same PCR primers (although this need not be required). This amplification results in a sample that contains amplified second nucleic acid sequence 111 and amplified first nucleic acid sequence 122. The second nucleic acid sequence will be hybridized to the complementary second nucleic acid sequence and the first nucleic acid sequence will be hybridized to the complementary first nucleic acid sequence. While the amount of the second nucleic acid sequence has been amplified at this point, the amount of the SNAS is still relatively minor compared the amount of the FNAS. The PCR products are then melted and hybridized together in step 30 forming small amounts of a heteroduplex 30 and relatively larger amounts of the homoduplex 120.

Following this, the heteroduplexes and homoduplexes are circularized in step 40 to produce a circularized heteroduplex 140 and a circularized homoduplex 125. Then an enzyme is used which recognizes a mismatch in heteroduplexed DNA and cuts next to the duplex, as shown in step 50. In some preferred embodiments, this enzyme is Endo V, which cuts one to two base pairs from a mismatch. This cutting of the CHET 140 creates a duplex 150. Preferably the duplex has sticky ends 151 and 152. Following this, a collection of binding moiety nucleic acid sequences are provided, each having different ends (e.g., having degenerate ends as a group) so that at least one will be readily ligated into the cut CHET (or duplex 150) in step 60, again circularizing the molecule.

The resulting binding moiety duplex 160 contains a binding moiety allowing manipulation of the solution and sample with respect to the BMD 160. At this point, the binding moiety duplex 160 can optionally be purified in step 80a by binding to a purifying moiety, which can be, for example, associated with beads in an affinity column. Alternatively, the process can continue by cutting the binding moiety duplex 160 in step 70 with a restriction enzyme, which recognizes a site in the BMNAS, but cuts external to the BMNAS, in the first and second nucleic acid sequences. In some embodiments, this restriction enzyme cuts the first and second nucleic acid sequences so that there is a sufficient amount of sequence remaining to identify the original first or second nucleic acid sequences (e.g., there are bar codes 171a and 171b).

At this stage, if the solution has not yet been purified, then one can collect the BMD with a purifying moiety to remove the CBMD 170 from the sample (step 80b, not shown in FIG. 10).

Once the cut binding moiety duplex 170 is created and sufficiently free from the CHOM, a first and a second PCR primer site (adapters 81 and 82) can be added to the CBMD 170. These two primer sites 81 and 82 can then be used for emulsion PCR on the CBMD 170. Following this, the PCR amplified product can be sequenced via a highly parallel non-electrophoretic sequencing technique (e.g., SOLiD™ (Supported Oligo Ligation Detection) highly parallel non-electrophoretic sequencing) or another appropriate sequencing method. The following section discusses various embodiments of each of the above disclosed steps in greater detail.

Gathering a Sample for Enrichment

It will be appreciated by one of skill in the art that a number of samples and methods for gathering samples can be used, the selection of which will depend upon the objective, the nature of the sample and what one wants to examine the sample for. The sample can contain any form of nucleic acid sequence (e.g., DNA, cDNA, RNA, mRNA, miRNA, etc.). In some embodiments, one type of nucleic acid can be converted to another for convenience, for example, where a mismatch dependent enzyme is used that only works in DNA, an RNA sample can be converted to DNA.

As noted above, in some embodiments a sample will be collected and the nucleic acid sequences of possible interest amplified. As an initial enrichment and amplification step, in some embodiments PCR primers can be selected to target a first nucleic acid sequence and a second nucleic acid sequence. It will be appreciated by one of skill in the art that the same set of primers can be selected to allow for amplification of both the first nucleic acid sequence and the second nucleic acid sequence. Thus, a single set of primers can effectively amplify both groups 121, 122 and 111, 112. As will be appreciated by one of skill in the art, the primers can be relatively specific for the first and second sequences. For example, in embodiments in which one knows that a particular gene contains a SNP, a primer specific for that gene can be used. In embodiments in which the sequence or gene to be enriched or characterized is not initially known, or where numerous genes or sequences are to be looked at, primers that bind with a greater frequency to the nucleic acids in the sample can be used. For example, shorter, universal, degenerate, and/or numerous primers can be used to allow for larger numbers of nucleic acids to be simultaneously amplified and then run through the present methods. In some embodiments, the initial sample will be purified so that it effectively contains primarily the nucleic acid sequences (e.g., DNA, RNA, miRNA, etc.) in solution; however, this is not required.

In some embodiments, the samples are collected as part of a diagnostic, for example, for determining if a tissue sample contains a nucleic acid sequence associated with cancerous cells. However, the sample can also be taken from healthy or presumably healthy individuals in order to characterize any, some of, or all of the variation within the individual's genome. For example, the present technique could be used to generally identify SNPs or other genetic variations that an individual has. Additionally, the sample, and the resulting amplified PCR product within the sample, can be collected and amplified with a specific gene of interest in mind. Thus, a specific PCR primer can be used to amplify two nucleic acid sequences (the first and second nucleic acid sequences) that are associated with a single gene or nucleic acid sequence. Additionally, as described herein, in some embodiments, the original sample need not have both a first and a second nucleic acid sequence. Thus, in some embodiments, the initial PCR amplification only amplifies a first or a second nucleic acid sequence, with the other sequence being added to form a heteroduplex at a later point in time.

A large number of FNASs and SNASs can be present and processed through these methods simultaneously. The various species of FNASs and SNASs need not be the same sequences or from same gene, although they can be. In some embodiments, a single species of FNAS is present and multiple species of SNASs are present that, apart from the mismatches, are identical to the species of FNAS and able to form a heteroduplex with the FNAS. In some embodiments, the various species of FNAS and SNAS, while from a single gene (or nucleic acid sequence), are from different parts of the gene (or nucleic acid sequence). In some embodiments the various species of the FNAS and SNAS are from different genes and/or different nucleic acid sequences. In some embodiments, the various species of FNASs are from a human genome or from a standard sample. The standard sample can include a collection of genes or nucleic acid sequences that are considered to belong to healthy individuals and therefore represent "normal sequences." A large number of various species of FNAS and SNAS are contemplated, e.g., 2-5, 5-10, 10-20, 20-50, 50-100, 100-200, 200-500, 500-1000, 1000-5000 or more different FNAS and/or SNAS species are contemplated. In some embodiments, an entire genome is processed though the present methods. In some embodiments, the genome is human, mammal, plant, bovine, porcine, fish, etc. As will be appreciated by one of skill in the art, some of the present embodiments are especially useful when the genome of the organism is known.

In some embodiments, both the FNAS species and the SNAS species come from the same individual or sample, such as a biopsy to test for a cancerous mutation. When a sample is collected from an individual, as in a biopsy it can contain both any variations that an individual might have, as well as any variations between the healthy and "sick" (e.g., cancerous) cells. As will be appreciated by one of skill in the art, in such an embodiment, there is effectively an internal subtraction occurring regarding SNPs or other variations in that individual's genomic sample that could be different from the general populace. Because of this, the primary mismatches that occur will be from variations in the nucleic acid sequences between the cancerous cells and the healthy cells. Of course, an initial PCR step 20 can also be used to effectively eliminate any other background nucleic acid sequences that can also be present in the sample.

As will be appreciated by one of skill in the art, in some embodiments, the present technique can be applicable to various diagnostics and will be effective as long as heteroduplexes can be formed that involve a target nucleic acid sequence that would be considered diagnostic.

Additionally, in some embodiments, some of the disclosed methods can be used in order to determine genetic differences between a first and a second sequence. These genetic differences can be of any type for example, insertions, deletions, replacements, etc., and can be a difference within a tissue, a sample (such as in a biopsy), or differences between individuals for the same nucleic acid sequence, such as a gene. For example, in some embodiments, some of the present embodiments can be used to identify a single nucleotide polymorphism in an individual.

Formation of a Heteroduplex

As noted in the above description and in FIG. 2, in many embodiments, the original sample already includes a mixture of a first nucleic acid sequence and a second nucleic acid sequence. As noted above, these nucleic acid sequences are complementary except for one or more bases that are involved in the formation of a mismatch. In such a case, following the above PCR amplification (if desired), a larger number of homoduplexes of first nucleic acids 120 and homoduplexes of second nucleic acids 110 are present. The strands of the homoduplexes 110 and 120 are separated and allowed to reanneal to form both the homoduplexes of the first nucleic acid sequences 120 and heteroduplexes 130 that include the second nucleic 111 and the first nucleic acid 122, as well as a mismatch 131.

As will be appreciated by one of skill in the art, the separation of the strands can be achieved in any number of ways, such as heating or altering salt concentrations. However, as relatively rapid reannealing of the strands can be desired, one useful way of separating and reannealing is through heating and cooling of the sample.

In some embodiments, the mismatch in the heteroduplex is a single base pair mismatch. However, as will be appreciated by one of skill in the art, the present technique is not limited to such embodiments. In some embodiments the mismatch can include any length or amount of nucleic acids. For example, mismatches of 1, 2, 3, 4, 5-10, 10-20, 20-30, 30-100, 100-200, 200-500 or more nucleic acids can occur in the heteroduplex 130. In some embodiments, the mismatch is not between two different bases, one on each strand, but is the presence of an additional base or the absence of a base between the two sequences.

As will be appreciated by one of skill in the art, the formation of the heteroduplexes 130 is a statistical probability given the large number of first nucleic acid sequences 122 and 121 and the relatively small number of second nucleic acid sequences 111 and 112. Because of this, the likelihood that a second nucleic acid 111 and a complementary second nucleic acid 112 will find one another and reanneal to form a homoduplex of second nucleic acids 110 is relatively low.

In some embodiments, only a single mismatch site 131 is present in any given heteroduplex. In embodiments in which more than one is present, multiple cutting can occur in later steps. This can be controlled for by examining the resulting products and selecting those with sequences that are consistent with known nucleic acid sequences in a host's genome. As will be appreciated by one of skill in the art, in such embodiments, it can be useful to have longer bar codes on each side of the CBMD, as a single bar code may be required to identify the original nucleic acid sequence(s).

Circularization

Following the formation of the heteroduplex 130, the nucleic acid sequences in the sample are circularized by ligation of the termini. Circularization can be achieved in any of a variety of manners. In some embodiments, circularization can be performed by some of the methods disclosed in U.S. Pat. No. 6,054,276 to Steven Macevicz and/or in Smith et al. (U.S. Publication US 2006/0024681), the relevant portions of which are herein incorporated by reference in their entireties. However, as will be appreciated by one of skill in the art, any method of circularization can be used.

While there is no need to circularize the homoduplexes 120 in all embodiments, they are typically circularized as a natural result of circularizing the heteroduplexes in the sample.

As will be appreciated by one of skill in the art, an advantage of circularizing the heteroduplexes is that the nucleic acid sequence will stay together if the heteroduplex is cut elsewhere. This can be especially advantageous to maintain the integrity of the nucleic acid sequence, especially if it is near one of the ends of the heteroduplex. Additionally, circularization allows for specific ligation in later steps. This circularization not only allows for maintaining the sequence's integrity (that is, a single FNAS stays a single FNAS, instead of two half FNAS linked together) but it also allows ligation near the mismatch. As a result, a very short length of nucleic acid sequence can be used to identify the FNAS and SNAS as well as the mismatched base pairs.

As will be appreciated by one of skill in the art, while all of the heteroduplexes can be circularized, in some embodiments, only a fraction are circularized (e.g., circularization need not occur to 100% of the heteroduplexes). While this could complicate issues during the ligation step, the arrangement of the cut BMD (that is, bar code sequences on either side of a BMNAS) will be sufficient to allow one of skill in the art to identify which of the sequences are representative of the original sequence.

In some embodiments, circularization is achieved through the use of CAP linkers (or adaptors). These linkers can be ligated onto the homoduplexes and heteroduplexes and then the linkers can be ligated together to form a circularized product.

Circularized molecules are resistant to some nucleases, thereby allowing for an optional step where one can degrade unwanted non-ciruclarized molecules though the use of these nucleases.

Selective Cutting of Heteroduplexes

Once the heteroduplexes 130 are circularized into circular heteroduplexes (CHET) 140, the solution is treated with a mismatch dependent enzyme. There are a variety of examples of mismatch dependent enzymes that can be used. In some embodiments, any enzyme that fully cleaves both strands of nucleic acid sequence at a heteroduplex can be used. In some embodiments the enzyme is Endo V. Additional forms of mismatch dependent enzymes are disclosed in U.S. publication No. 2003/014,8283 published Aug. 7, 2003 to Frances Barany et al., which discloses multiple enzymes that cleave at the mismatch sites. Further discussion of such enzymes include the teachings of Yao et al. entitled "Strand-specific cleavage of mismatch containing DNA by Deoxyinosine 3' Endonuclease from *E. Coli*" in the *Journal of Biological Chemistry* 1994, Vol. 269, pp. 31390-31396 and Huang et al. entitled "Endonuclease/Ligase Mutation Scanning Method Specially Suited for Analysis of Neoplastic Tissue," 2002 in *Oncogene*, Vol. 21, pp. 1909-1921, as well as "SNP Discovery in Pole Samples with Mismatched Repair Detection," Fakhrhi-Rad et al. in *Genome Research,* 2004, Vol. 14, pp. 1404-1412 and Yao et al. entitled "Cleavage of Insertion/Deletion Mismatches Flap and Pseudo-Y DNA Structures of Deoxyinosine 3' Endonuclease from *E. Coli*," in the *Journal of Biological Chemistry* 1996 Vol. 271, pp. 30672-30676; He et al. "Deoxyxanthosine in DNA is Repaired by *E. Coli* Endonuclease V," in *Mutation Research*, Vol. 459, pp. 109-114 in 2000; Malek et al. Mismatch repair detection (MRD): high-throughput scanning for DNA variations. Human Molecular Genetics 10:1657-1664 (2001); Cotton et al., U.S. Pat. No. 5,958,692 (T4 endonuclease VII); Babon et al. U.S. Pat. No. 5,851,770; and Barany et al. PCT Pub. No. 2006/023919. These references are incorporated herein in their entirety.

Indeed, in some embodiments, any form of mismatch dependent cutting can be used (e.g., the cutting need not be enzyme based). For example, resolvase cleavage can be used, as disclosed in Cotton et al. U.S. Pat. Nos. 5,698,400 and 5,958,692, and chemical cleavage can be used, as described in U.S. Pat. No. 5,972,618 to Bloch. In general, methods designed to detect nucleic acid mismatches in a heteroduplex can contain enzymes or processes that can be applied in some of the present embodiments. These methods include RNAse A digestion, chemical cleavage, as well as PCR- and primer extension-based detection methods (reviewed in Cotton, Curr. Opinion in Biotech. 3, 24 (1992)). The resolvases (e.g. X-solvases of yeast and bacteriophage T4, Jensch et al. EMBO J. 8, 4325 (1989)) are nucleolytic enzymes capable of catalyzing the resolution of branched DNA intermediates (e.g., DNA cruciforms) which can involve hundreds of nucleotides. In general, these enzymes are active close to the site of DNA distortion (Bhattacharyya et al., J. Mol. Biol., 221, 1191, (1991)). T4 Endonuclease VII, the product of gene 49 of bacteriophage T4 (KIeff et al., The EMBO J. 7, 1527, (1988)) is a resolvase (West, Annu. Rev. Biochem. 61, 603, (1992)) which was first shown to resolve Holliday-structures (Mizuuchi et al., Cell 29, 357, (1982)). T4 Endonuclease VII has been shown to recognize DNA cruciforms (Bhattacharyya et al., supra; Mizuuchi et al., supra) and DNA loops (Kleff et al., supra), and it may be involved in patch repair. Bacteriophage T7 Endonuclease I has also been shown to recognize and cleave DNA cruciforms (West, Ann. Rev. Biochem. 61, 603, (1992)). Eukaryotic resolvases, particularly from the yeast *Saccharomyces cerevisiae*, have been shown to recognize and cleave cruciform DNA (West, supra; Jensch, et al., EMBO J. 8, 4325 (1989)). Other nucleases are known which recognize and cleave DNA mismatches. For example, S1 nuclease is capable of recognizing and cleaving DNA mismatches formed when a test DNA and a control DNA are annealed to form a heteroduplex (Shenk et al., Proc. Natl. Acad. Sci. 72, 989, (1975)). The Mut Y repair protein of *E. coli* is also capable of detecting and cleaving DNA mismatches. However, the Mut Y repair protein is only capable of detecting 50% of the total number of mutations occurring in a mutant DNA segment (Lu et al., Genomics 14, 249, (1992)). The only important aspects for the enzyme, chemical process, or general cutting step are that the cutting be mismatch dependent, and that both strands (the first and second nucleic acid sequences) are cut. If both strands are not cut, then the ligation step described below must be adjusted accordingly.

In some embodiments, an enzyme is used that cleaves in a known relative location upstream or downstream of the base pair mismatch, thereby allowing one to identify, with greater certainty, the location of the mismatch by identifying the location of the cut.

Cutting the CHET results in formation of the duplex 150. For the subsequent steps, it is preferred that the circularized heteroduplex 140 be completely cleaved, resulting in a linear duplex. As will be appreciated by one of skill in the art, nonspecific nicks can occur during the processing but need not be problematic.

In some embodiments, the presence of these nicks should not adversely impact the results of this method. In previous techniques, which nick nucleic acid sequences, melt the strands, and run them separately on a gel, the nicks can result in a false positive for mismatches. However, in embodiments in which complete cutting of the heteroduplex occurs, nicks in the DNA need not result in false positives, as the strands can stay annealed through the processing. Indeed, to reduce the likelihood of false positives later in the process, a nick repair step can be performed, although it is not required.

A minor or insignificant amounts of nonspecific cutting may occur to the homoduplexes; however, a significant amount of the cleaved molecules in nucleic acid sequences and in the solution or duplexes 150 will be from the circularized heteroduplex 140.

The cleavage of the mismatch can leave either a sticky end or blunt end. Cleavage by Endo V leaves a sticky end on the cleaved duplex. As noted below, sticky ends can be addressed through the use of degenerate endings on a BMNAS. In some embodiments, it may be advantageous to blunt the ends, thereby removing the need for degenerate ends on the BMNAS. Blunting can be achieved in any number of ways, for example end-filling or removal of the sticky ends.

In some embodiments, one can increase the likelihood that both strands of the CHET are cut by the endonuclease by including an additional enzyme to make certain that both nucleic acid strands are cut. For example, in some embodiments, S1 endonuclease or manganese can be included to assist with the cutting. In some embodiments, an assistant enzyme will only aid in the cutting of the heteroduplex and will not perform the cutting without the heteroduplex dependent endonuclease.

Ligation of Binding Moiety

As described above, following the cleavage of the circularized heteroduplex to form the duplex 150, one can then ligate a binding moiety nucleic acid sequence 155 into the duplex to create a binding moiety duplex (BMD) 160 in step 60.

In some embodiments, the binding moiety 156 can be associated with the duplex 150 through the addition of a nucleic acid sequence 154, which is attached to the binding moiety 156, optionally through a linker 157. The binding moiety nucleic acid sequence 155 can include a number of components although the only required part is the binding moiety itself and a means of attaching it to or into the duplex 150.

In some embodiments, only a BM 156 is associated with the duplex 150. For example, this could occur where the binding moiety is a nucleic acid sequence that can be directly ligated into the duplex. An example of such a BM 156 is a DNA or RNA aptamer, thereby allowing direct ligation of a BM by which the duplex can be manipulated. A nucleic acid sequence that can be bound by an antibody can also be used. In other embodiments, the binding moiety is not a nucleic acid sequence and the binding moiety is associated with the duplex 150 without the use of a nucleic acid sequence 154. For example, an antibody to a sequence in the duplex 150 can be used or any method for attaching probes to terminal nucleic acids can be used. However, in many embodiments, the section to be added to the duplex will include a nucleic acid sequence and a binding moiety already associated with the sequence. As will be appreciated by one of skill in the art, in some embodiments, it can be valuable to ligate the cut ends of the duplex back together, as this has a greater likelihood of keeping relevant sequences (as well as the bases involved in the mismatch) together for further processing later. For example, this will allow for the formation of bar codes and will keep the sequences consistent throughout the processing.

In some embodiments, the binding moiety nucleic acid sequence 155 includes a nucleic acid sequence 154, optional restriction sites 158a and 158b, and optional degenerate ends 153a and 153b. As noted above, the degenerate ends 153a and 153b denote the use of a number of different binding moiety nucleic acid sequences, each binding moiety nucleic acid sequence having a different combination of nucleic acids at the ends. The number of degenerate nucleic acids at the end can be any number and is frequently one or two on each end (e.g., in situations in which Endo V is used). As such, a method involving binding moiety nucleic acid sequences 155 with degenerate ends 153a and 153b can involve 16 degenerate binding moiety nucleic acid sequences, each one having a different combination of nucleic acids at each end. With 16 "different" BMNASs (where the only difference is in the terminal nucleic acids 153a and 153b), all possible sticky ends 151 and 152 resulting from step 50 (assuming that there is a single nucleic acid overhand) can be accounted for. In some embodiments, more nucleic acids are present on each sticky end and as many as 256, 1,024, or more degenerate ends are used. For example, in situations involving Endo V as the mismatch dependent enzyme, either one or two nucleic acids can be included in the overhangs 151 and 152. If these overhangs remain, then degenerate BNASs of 155 can be covered by either 16 or 256 variations.

In some embodiments, the binding moiety nucleic acid sequence 155 includes additional restriction sites that allow for further processing. Additional restriction sites can be located near the distal regions of the BMNAS 155 and in some embodiments are external to the binding moiety 156 and to the nucleic acid sequence 154, as shown in FIG. 6. In some embodiments, the restriction sites will cleave distally to the binding sites (as shown in FIG. 7). In a preferred embodiment, either type IIs or type III restriction sites and enzymes are used. Some enzymes and sites can include FOCK I, EcoP I, MME I, and/or type III, ATP-dependent restriction enzymes and sites. In alternative embodiments, one could also cleave by shearing in order to cut the binding moiety duplex 160. Preferably cutting of the binding moiety duplex leaves approximately 20 nucleic acids on either side of the mutated base. In a preferred embodiment, approximately 40-30, 30-20, 20-10 nucleic acids are present on each end of the CBMD 170 that belong to the original FNAS and SNAS.

While the same restriction site can be used for 158a and 158b, they need not be the same. Additionally, while the BMNAS can include the nucleic acid sequence 154, the linker 157, the BM 156, restriction sites 158a and 158b, and degenerate ends 153a and 153b, as noted above, not all of these aspects need to be present in every embodiment. Depending upon the end goal of the employed method, any combination of the above may be present. Thus, in some embodiments, only a BM 156 is used in step 60, which need not actually circularize the duplex 150. Similarly, in some embodiments, a BM 156 is used with degenerate ends 153a and 153b, without the nucleic acid sequence 154 or the restriction sites. In some embodiments, a BM 156, linker 157, restriction sites 158a and 158b and degenerate ends 153a and 153b are used, without the nucleic acid sequence 154. As will be appreciated by one of skill in the art, each of the possible combinations have various advantages, which will be clear to one of skill in the art, in light of the present disclosure.

The sticky ends 151 and 152 on the duplex 150 need not be kept in all situations, especially in embodiments in which the actual identity of the point mutation need not be known. Thus, in some embodiments, the sticky ends can be removed to form blunt ends in the duplex 150. In such embodiments there is no need for the use of degenerate ends on the binding moiety nucleic acid sequence 155. Additionally, as will be appreciated by one of skill in the art, for the purposes of enriching a particular species over others, it is not necessary that the binding moiety nucleic acid sequence contains restriction sites 158a and 158b. Thus, in some embodiments, the binding moiety nucleic acid sequence 155 includes only a binding moiety 156. In other embodiments, the binding moiety nucleic acid sequence 155 is not used and instead the enrichment of the duplex over the circularized homoduplexes 125 is achieved through the selection of cleaved CHETs 140 (duplexes 150) over circularized homoduplexes 125.

The term "binding moiety" (BM) refers to a molecule that can bind, be bound to another molecule, or both, with sufficient strength so that the BM and a molecule associated with the BM (e.g., a nucleic acid sequence 154 or duplex 150) can be separated, to some extent, from those nucleic acids sequences that are not associated with a BM 156. In some embodiments this means that the BM 156 is capable of interacting with a purifying moiety (PM) 166 to an extent sufficient to allow some purification and/or enrichment of the BM 156. However, the BM need not always require a purifying moiety. For example, a BM 156 can be a magnetically controllable particle, allowing for the subsequent purification of the BM through the use of a magnetic field.

In some embodiments, the BM 156 can allow the complete removal from solution of all molecules covalently associated with it. In other embodiments, the BM 156, when paired with a PM 166, allows for an effective amount of the molecule associated with the BM 156 to be removed from a sample via the removal of the PM 166 from the sample. For example, removal of 100% to 1% or less, for example, 100-99, 99-95, 95-90, 90-80, 80-70, 70-50, 50-30, 30-20, 20-10, 10-1 percent or less of the BM 156, and thus, the molecule associated with the BM 156, can be sufficient to allow the compositions and methods disclosed herein to perform as desired. The required amount will be determined according to the teachings herein and the knowledge of one of ordinary skill in the art, as appropriate for a particular situation.

Any molecule with the desired particular characteristics can be useful as a BM. In some embodiments, the BM 156 should not interfere with the optional aspects in the SMNAS. The BM 156 can bind sufficiently tightly and with a sufficiently long duration so as to allow the BM 156 to bind to, or be bound by, the PM 166 and for both to be removed from the sample, as well as any molecule associated with the BM. As will be appreciated by one of skill in the art, the molecules associated with the BM can vary depending upon the embodiment. Additionally, the BM 156 need not be covalently attached to the associated molecule as long as the interaction between the BM and the associated molecule (e.g., nucleic acid sequence 154) is sufficiently stable so as to allow removal of the associated molecule from the sample, through the use of the BM 156. Examples of such a molecule include biotin, avidin, streptavidin, epitopes and paratopes from antigens and antibodies. As will be appreciated by one of skill in the art, this list includes options for both the BM and PM and will be paired appropriately.

Optional Purification

After the insertion of the binding moiety nucleic acid sequence 155 into the duplex 150 to form the binding moiety duplex BMD 160, only those nucleic acid sequences which contain the mismatch and thus initially contain the second nucleic acid sequence will be associated with the binding moiety 156. At this point, the second nucleic acid sequence 111 can be purified or enriched relative to the first nucleic acid sequence 122 simply by collecting the binding moiety 156 and its associated components (including the nucleic acid of interest).

As noted above, this enrichment can be carried out using a purifying moiety 166 which binds to the binding moiety 156. As will be appreciated by one of skill in the art, the identity of the purifying moiety and the binding moiety can vary depending on a number of factors. In some embodiments, the binding moiety is biotin and the purifying moiety includes streptavidin, optionally associated with magnetic beads. However, the identity or particular aspects of the purifying and binding moieties are not crucial, as long as the binding moiety can be associated with a nucleic acid sequence and as long as the purifying moiety (if required) can effectively bind to the binding moiety with a sufficient degree of specificity and strength to allow the separation of the binding moiety duplex 160 from the circularized homoduplex 125. As will be appreciated by one of skill in the art, the purification step can occur at various stages once the binding moiety 156 has been associated with the duplex 150. Thus, in some embodiments, purification occurs at a later stage, e.g., after a cleavage step of the binding moiety duplex 160.

In some embodiments, where a BM 156 or BMNAS 155 is not associated with the duplex, enrichment of the duplex 150 over the homoduplexes 125 can be achieved by any method that will allow the separation of circularized nucleic acid sequences from linearized nucleic acid sequences. Thus, in some embodiments, the duplex 150 and homoduplexes 125 can be separated on a gel or molecules that bind to linearized nucleic acid sequences but not circularized sequences can be used.

In some embodiments, one ligates a biotin to a termini and performs a reverse purification (removal of waste as opposed to removal of target).

In some embodiments, the selection of circularized DNA over linear DNA is achieved via an enzyme with such a selectivity. For example, an enzyme such as Bal31 exonuclease, which cannot digest circular DNA but can digest termini, can be used in a selection step as well.

Cleavage of Binding Moiety Duplex

In some applications the identity of a gene or sequence which involves a variation or base pair mismatch is sought. In some embodiments, it is also important to identify the particular difference between the first nucleic acid sequence and the second nucleic acid sequence. One way of resolving these issues is to sequence all of the nucleic acid sequence in the duplex 150. However, the ease with which this process can be achieved can be highly variable as it will depend, in part, upon the size of the first and second nucleic acid sequences.

However, it is possible to achieve the desired results without having to sequence the entire sequence of the FNAS 122 and SNAS 111 in every situation. In particular, in situations in which a genome or large amount of an organism's (or related organism's) sequence is already known, a shorter length of sequence can be used to identify the FNAS and SNAS. That is, a bar code (or paired tag) 171*a* and 171*b* can be used to identify what sequence, (for example, what gene in the organism) the bar code (and thus the FNAS and SNAS) are part of. Not only does this reduce the amount of sequencing that would otherwise be required, but it allows for sequencing techniques that might not otherwise be as applicable. In particular, parallel sequencing techniques that are optimal in their processing powers over relatively short distances can be used (discussed in more detail below). While these techniques can have advantages over traditional, longer run sequencing techniques, they frequently present additional issues when used on longer sequences. Thus, in situations in which one has a library or genome with which to compare a bar code present on an FNAS or SNAS to, and thereby identify the FNAS and SNAS, reducing the amount of nucleic acid sequence involved in the subsequent sequencing steps allows for the use of these parallel sequencing techniques.

As such, in some embodiments the majority or at least a section of the first and second nucleic acid sequences is removed from the binding moiety duplex 160 in order to take advantage of these alternative sequencing methods. In such embodiments, a small amount of the first and second nucleic acid sequences 171*a* is retained as bar codes, in order to identify the first and second nucleic acid sequences.

This cutting step can be achieved through the use of the restriction cites 158*a* and 158*b* contained within the BMNAS 155. As noted above, in some embodiments, these restriction sites result in the cleavage of nucleic acids distally from the actual site. While a variety of restriction enzymes and restriction sites can be used type IIs or type III restriction sites and enzymes are used in some embodiments, for example, FOCK I, EcoP I, MME I, and ATP-dependent restriction enzymes. In some embodiments, an EcoP15II site and enzyme is used to cut the binding moiety duplex 160 to form the cut binding moiety duplex 170. As EcoP15I cuts approximately 25 bases from the site, there will be approximately 25 nucleic acids remaining on either side of the EcoP15I binding site.

The result of the cut(s) is shown in FIG. 7. Cutting of the BMD 160 results in a linear duplex, the cut BMD 170, which includes "bar codes" or "paired tags" 171a and 171b. The cut binding moiety duplex further includes the mismatched base-pair (which can be a mutation) at 131c and 131d. As such, the cut binding moiety duplex CBMD 170 allows for the relatively short sections of the original nucleic acid sequences 111 and 122 to be used to adequately identify the sequence and still allows one to identify the point mutations 131a, 131b if desired. In light of this, while the binding moiety duplex 160 need not be cut, it can be especially advantageous to cut the binding moiety duplex 160 not only once but twice to eliminate an excess amount of the first nucleic acid sequence 122 and second nucleic acid sequence 111, shown in FIG. 7 as item 172. In a preferred embodiment, the length of the bar codes 171a, 171b are less than 200 nucleotides, for example 200-100, 100-50, 50-40, 40-30, 30-20, 20-10, or fewer nucleic acids in length.

In some embodiments, the method is performed with a sample from an organism in which all of the genes or sequences of interest are already known or identified. Thus, the shortened nucleic acid sequences or bar codes can be used for ready identification by comparing the sequence of the bar codes to the known genome to identify what gene the FNAS and/or SNAS are part of.

In some embodiments, the cleaved ends of the CBMD are sticky and, if further processing is desired, polishing of the ends can be beneficial. Thus, optionally, a polishing step can be performed on the CBMD, if, for example, a subsequent ligation step is to be performed that will involve the CBMD.

If the homoduplex was not previously separated from the heteroduplex, this enrichment/purification step can be performed following the cutting step 70. Performing the step at this point provides an added benefit of not only removing the homoduplexes 125, but also the excess nucleic acid sequences 172. This process is generally shown in FIG. 8, in which a purifying moiety 166 is used to bind to the BM 156, which is in solution with the homoduplex 125 (and possibly the excess nucleic acid sequences 172) in solution 101. The purifying moiety 166 can then be transferred (in step 80b) to another container, along with the associated BM 156 and duplex 170, resulting in a solution 102 in which the amount of SNAS has been enriched compared to the initial amount of FNAS. As will be appreciated by one of skill in the art, any separation of the PM 166 from the original solution 101 will be adequate. Thus, in some embodiments the PM is immobilized to beads and the solution 101 is simply run over the beads, which are then rinsed, resulting in the removal of the homoduplexes 125. Similarly, the PM 166 can be associated with magnetic particles and removed from the solution 101 through the application of a magnetic field.

Adapters for the CBMDs and Amplification

While one could characterize the remaining sections of the FNAS and SNAS following the cutting 70 of the BMD 160, in some embodiments it is advantageous to further amplify the amount of the cut binding duplex 170 through a further amplification step. One method by which this can be achieved is shown in FIG. 9.

In some embodiments, adapters 181 and 182 can be added to either side of the cut binding moiety duplex 170 to enable further amplification of the cut binding moiety duplex 170 and in particular the mutation or source of the mismatch. In some embodiments, adapters 181 and 182 are PCR primer sites added in steps 81 and 82. The selective addition of asymmetrical adaptor can be achieved in a variety of ways. In a preferred embodiment, this is achieved as disclosed in U.S. application Ser. No. 11/338,620, entitled Asymmetrical Adapters and Methods for Constructing Amplified Paired End Libraries for Genome Sequencing, incorporated herein by reference in its entirety. In some embodiments, adapters 181 and 182 are PCR primer sites and are two different sequences.

In addition to using specific PCR priming sites, any method or process allowing for amplification of the nucleic acids can be used. For example, in some embodiments, one could use a terminal transferase which can provide a polyadenylation tail of approximately 20 base pairs on either side of the CBMD 170. This polyA tail can then be used as a site for amplification of the cut binding moiety duplex 170.

Following the addition of adapter 181 and adapter 182, one can then add primers to the adapters and perform a PCR amplification.

In a preferred embodiment, one uses emulsion PCR in order to rapidly amplify the large number of various CBMDs 170. Such techniques are well known in the art and are discussed in Dressman et al., "Transforming Single DNA Molecules in Fluorescent Magnetic Particles for Detection and Enumeration of Genetic Variations," PNAS, Vol. 100, pp. 8817-8822 (2003) and in Leamon et al., PCT Application WO 2005/003375 entitled "Methods of Amplifying and Sequencing Nucleic Acids." In some embodiments, the emulsion PCR will involve magnetic beads, to which oligonucleotides (primers) are associated (perhaps biotin/streptavidin, although this can depend upon the actual BM used). The beads are added to an aqueous mixture that has all of the necessary ingredients for PCR, with the CBMD 170, and the components are mixed with an oil/detergent mix to form microemulsions, Ideally, each aqueous cell in the emulsion contains, on average, less than one template and less than one bead. The entire mixture is then temperature cycled as in a PCR amplification. When a bead and a template are in the same aqueous cell, the bead associated oligonucleotide will act as a primer.

In some embodiments, this is especially advantageous when a large number of various species of FNASs and SNASs are being examined simultaneously. In some embodiments, 1-5, 5-10, 10-50, 50-100, 100-500, 500-1000, 1000-5000 or more different species of nucleic acid sequences (or parts thereof) are examined simultaneously throughout at least some of these later steps in the above-described process. In some embodiments, the number is of various CBMDs that are being examined.

Following this step, the beads can be delivered to an array of a large number of reaction chambers such that a number of the reaction chambers include no more than a single bead. If desired, one can then perform a sequencing reaction simultaneously for each of the reaction chambers.

Characterization of the Mismatched Base(s)

Following the amplification of the adapter-containing cut binding moiety duplex 180, the remaining parts of the FNAS and/or SNAS, such as the bar code 171a and 171b and/or the actual bases involved in the mismatch 131c and 131d will typically be characterized. In some embodiments, this characterization will mean sequencing the amplified product. In some embodiments, the characterization involves simply identifying the sequence or location of the first or second nucleic acid sequences in a genome, for example using the bar codes. This can allow one to identify a possible gene or other sequence involved in the mismatch, which can have a relevant phenotype of interest.

In some embodiments, the actual site and nature of the difference between the FNAS and SNAS can also be determined by identifying the location of the insertion of the binding moiety nucleic acid sequence 155. Alternatively, simply sequencing the two strands of the product 180 can provide two separate sequences, allowing identification of the bases involved in the mismatch. In characterizing the mismatch, one can simply identify a gene or sequence in which the mismatch occurs, identify the position or location of the nucleic acid in which the mismatch occurs, or in some embodiments, identify the actual nucleic acid difference by comparing the first nucleic acid sequence and the second nucleic acid sequence (by examining the sequence results). As noted above, this difference could be more than one nucleic acid and can include up to any number of nucleic acids between the first and second nucleic acid sequences.

Parallel Sequencing

These methods can be applied in situations in which massively parallel sequencing is advantageous or desired. For example, some embodiments can be useful when a large number of different genes or large number of various sections of the same or different genes are present. Thus, in embodiments in which there are multiple species of FNASs or SNASs the adaptor containing CBMD 180 can be characterized by a parallel sequencing method.

Sequencing techniques that are optimized for sequencing large numbers of relatively short strands of nucleic acid sequences are use for some embodiments. For example, when a final product involves a bar coded nucleic acid sequence (without the excess sequence 172), these products can be run through a faster, optionally more accurate, sequencing method than traditional longer run sequencing techniques. This use has the added advantage of not only enhancing or detecting particular targets from a large variety of possibly very similar sequences, but doing so in a very efficient manner because only a short segment will need to be sequenced to identify the nucleic acid sequence and the particular nucleic acid(s) responsible of the mismatch.

As will be appreciated by one of skill in the art, there are a variety of parallel sequencing techniques that could be used. For example, in some embodiments, the technique used involves sequencing by oligonucleotide ligation and detection, disclosed in PCT Publication No: WO2006084132 to Kevin McKernan et al., herein incorporated by reference in its entirety. In some embodiments, DNA sequencing is achieved by parallel oligonucleotide extension, e.g., as described in U.S. Pat. No. 5,750,341 to Macevicz et al., and U.S. Pat. No. 6,306,597 to Macevicz et al., both of which are herein incorporated by reference in their entireties, can also be used. Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803) the 454 picotiter pyrosequencing technology (Margulies et al., 2005 Nature 437, 376-380; US 20050130173), the Solexa single base addition technology (Bennett et al., 2005, Pharmacogenomics, 6, 373-382; U.S. Pat. No. 6,787,308, U.S. Pat. No. 6,833,246), the Lynx massively parallel signature sequencing technology (Brenner et al. (2000). Nat. Biotechnol. 18:630-634; U.S. Pat. No. 5,695, 934, U.S. Pat. No. 5,714,330) and the Adessi PCR colony technology (Adessi et al. (2000). Nucleic Acid Res. 28, E87; WO 00018957), each of which is herein incorporated by reference in its entirety.

The following sections generally discuss additional aspects that are relevant to some of the various embodiments.

First and Second Nucleic Acid Sequences

The first and second nucleic acid sequences can be selected from a large number of possible sequences. Effectively, the only requirement for the two sequences is that the first and second nucleic acid sequences are capable of forming a heteroduplex together, wherein that heteroduplex contains at least one mismatch. In some embodiments, the heteroduplex only contains one mismatch allowing for a single cleavage point in the heteroduplex 130. Multiple cleavings, while possible, can complicate processes later. In some embodiments, the first nucleic acid sequence is a wild-type gene and the second nucleic acid sequence is a mutant gene where one wishes to identify whether or not the second nucleic acid sequence is present in the sample. In other embodiments, the first nucleic acid sequence is a mutant gene and the second nucleic acid sequence is a gene of interest, which one wishes to determine if it is present in a sample. In such an embodiment, the presence of the mutant nucleic acid sequence will be evident by the absence of the formation of a heteroduplex.

As will be appreciated by one of skill in the art, the first and second nucleic acid sequences can be DNA sequences and in some embodiments they are RNA sequences such as mRNA. As will be appreciated by one of skill in the art, as long as the techniques described herein or results from the method steps achieved herein are possible in the various types of the nucleic acid sequence, any form of nucleic acid sequence can be used. Thus, effectively, any nucleic acid sequencing capable of forming a heteroduplex and being cleaved at that base pair mismatch could benefit from the method described herein.

Subtractive Enrichment

As will be appreciated by one of skill in the art, many of the present embodiments are described as involving enhancement of a target sequence via the positive selection of the sequence over other sequences via a binding moiety. However, in some embodiments, the enhancement of the target sequence, or sequences, is achieved through the removal of other sequences from solution. For example, in some embodiments, sequences known to be present in a sample are removed via the addition of a sequence that will form a heteroduplex with the known sequence in the solution. The heteroduplex is then acted on as described above, to the stage of using the purifying moiety, at which point the known nucleic acid sequence is removed from the sample and the remaining nucleic acid sequence are thereby enriched (relative to the initial sample). Of course, one can then amplify the remaining nucleic acid sequence targets and then characterize the sequences in any number of ways. As will be appreciated by one of skill in the art, when known nucleic acid sequences are added as control sequences, the known sequences can be just a single nucleic acid sequence or the hybridized pair of nucleic acid sequences. Of course, the use of the hybridized pair, in excess of the amount of the nucleic acid sequence to be removed, will allow for greater purification, as it will ensure that more of the initial majority sequence is removed.

Libraries

In some embodiments, general primers are used on an initial sample so that a large amount of the sequences that contain mismatches in a sample are amplified. Effectively, these mismatches can be representative of differences between otherwise similar and/or identical nucleic acid sequences. For example, the differences can be due to differences that are internal to the genome, differences due to the presence of two different cellular populations (such as healthy cells and cancerous cells), or a difference due to a control sequence added to the sample. In some embodiments some or all, e.g., 100, 100-90, 90-80, 80-70, 70-60, 60-50, 50-40, 40-30, 30-20, 20-10, 10-1, 1-0.1, 0.1-0.001 percent or less, of the different nucleic acid sequences are amplified. As noted in Example 5, this can result in the selective amplification of all (or some) of the nucleic acid sequences that have mismatched base pairs in a sample. In some embodiments, at least one nucleic acid sequence is amplified, for example, 1-3, 3-5, 5-10, 10-20, 20-50, 50-100, 100-1000, 1000-10000 or more nucleic acid sequences are amplified by a disclosed method. This will not only allow one to detect those nucleic acid sequences present in small amounts in a sample, but can effectively allow for a library of all (or some) of the variations present in a sample. In situations where the sample is a genome, then it can allow for all (or some) of the variations of the genome to be identified. In some embodiments, only a portion of the initial or native nucleic acid sequence (which forms or serves as the template for the FNAS or SNAS) is amplified. In some embodiments, it is preferable to limit or select the size of the FNAS and SNAS to make other steps more efficient. While a large variety of sizes could be used, the FNASs and SNASs can be less than a million base pairs, for example, 1,000,000-100,000, 100,000-10,000, 10,000 to 1,000, 1,000-500, 500-250, 250-200, 200-150, or less in length.

In some embodiments, the use of an in vitro approach allows for parallel processing, of a sample. Thus, a single, or relatively few, sequencing runs can be used to determine if a sample possesses any one of a number of possible minor species nucleic acid sequences or any number of possible variant nucleic acid targets (such as a variety of SNPs).

In some embodiments, the step of circularization, followed at some point by the step of mismatch-dependent cleaving and insertion of a BM (perhaps via a BMNAS), allows for a process that reduces false positives due to nonspecific nicking of nucleic acid sequences by the mismatch dependent enzyme. This had been problematic for techniques that ran products from mismatch dependent cutting on gels in order to determine the site of the mismatch. By requiring the complete cleavage of the circularized nucleic acid sequence for the subsequent association of the BM, sequences that are merely nicked will not appear in the final sample, unless they are also fully cleaved to allow for the insertion of the BM.

In some embodiments, the removal of the excess nucleic acid sequence 172 allows for a more efficient method of sequencing and characterizing the mismatch. As some sequencing methods are most effective over relatively short distances, having the full length nucleic acid sequence can be problematic and result in incomplete or more complicated sequencing methods. By selectively adding restriction sites 158a and 158b (e.g., via the BMNAS) near the location of the base pair mismatch, one can readily produce shorter sequences, that, while long enough to allow identification of where the FNAS and/or SNAS come from in a genome or sample, is short enough to allow shorter run sequencing techniques to be fully exploited. Additionally, by adding the restriction sites close to the section that contains the mismatch, one can make certain that the mismatch itself is adequately identified.

The following section generally outlines various examples of some of the embodiments discussed above.

EXAMPLES

Example 1

Enrichment of a Nucleic Acid Sequence

A biopsy is preferred to obtain a sample from a patient. Then, PCR amplification on a p53 gene in the sample is performed. This PCR amplification increases the population of wild-type p53, as well as any variant or mutant p53 present in the biopsy sample.

The products from the PCR amplification are melted and reannealed to form homoduplexes and a possible heteroduplex of the p53 gene (if mutant is present). Following this, the amplified products are circularized to form circularized homoduplexes and circularized heteroduplexes. The circularized homoduplexes and heteroduplexes are treated with Endo V, cleaving the heteroduplexes close to the mismatch in the heteroduplex. Following this, a biotinylated binding moiety nucleic acid sequence (BMNAS) is ligated into the cut circularized heteroduplex. While a single BMNAS can be used (where the cleaved ends are blunted), typically a plurality of binding moiety nucleic acid sequences are used, such that there are degenerate ends on the BMNASs (usually covering all possible ends), making at least one BMNAS readily ligatable into the cut heteroduplex. The binding moiety nucleic acid sequence further includes an internal biotin. By collecting the BMNAS, through the use of streptavidin associated with magnetic beads, the nucleic acid sequence that is part of the base pair mismatch is enriched.

Example 2

Characterization of the Mismatched Sequence

The enriched nucleic acid sequence created in Example 1 can be further characterized in order to determine the precise nucleic acid(s) involved in the base pair mismatch. The process described in Example 1 is performed, although the binding moiety nucleic acid sequence in Example 1 includes two EcoP15I sites, one near each end of the binding moiety nucleic acid sequence. Following the ligation of this modified BMNAS, the binding moiety duplex is cut with a type III cutter, in particular EcoP15I, to form a cut binding moiety duplex, which is then purified from the circularized homoduplexes by binding the biotin fragments to streptavidin coated magnetic beads and collection of the magnetic beads.

Following this, two separate primer sites or asymmetrical adapters, one added to each end as P1 and P2, are attached to the cut binding moiety duplex (as detailed in U.S. application Ser. No. 11/338,620, incorporated by reference in its entirety). These primers sites can then be used for subsequent PCR amplification by emulsion PCR. Finally, the product of this PCR amplification is sequenced by oligonucleotide ligation and detection (as detailed in App. No. PCT Publication No: WO2006084132 to Kevin McKernan et al., incorporated by reference in its entirety) to identify the mismatched nucleic acid in the heteroduplex. The mismatch can be identified by comparing the resulting sequences and determining where a difference occurs between the sequence of the FNAS and the SNAS. Alternatively, the presence of the known nucleic acid sequence, inserted as part of the BMNAS, can be used to locate the mismatch, as it will be close to the base pair mismatch.

Example 3

Characterization without Identifying the Mismatch

As will be appreciated by one of skill in the art, the target sequence does not need to be sequenced in every situation. For example, in some embodiments, one may simply wish to know where a mismatch is or that a mismatch (and thus a variant sequence) is present.

First a PCR amplification is performed on a sample to amplify a sequence of interest. This PCR amplification increases the population of the control (FNAS) and the target (SNAS) sequences. The products from the PCR amplification are melted and reannealed to form homoduplexes and a possible heteroduplex if the SNAS is different from FNAS. Following this, the amplified products are circularized to form circularized homoduplexes and circularized heteroduplexes. The circularized homoduplexes and heteroduplexes are treated with Endo V, cleaving the heteroduplexes close to any mismatch. Next, the sticky ends of the cleaved product are blunted. This will eliminate the need for multiple forms of the BMNASs. Following this, a biotinylated binding moiety nucleic acid sequence is ligated into the cut heteroduplex (duplex). The BMNAS will contain the two restriction sites as described in Example 2. Processing and characterization of the sequence can continue as described in Example 2. Of course, as the base pair mismatch itself may be deleted, (e.g., by the blunting), one could be left with only the identity of the bar code sections surrounding the initial basepair responsible for the mismatch. However, this will be sufficient for identification of the site or general location of the mismatch.

In an alternative embodiment, the sticky ends of the duplex can be backfilled, thereby retaining the nucleic acids involved in the mismatch.

Example 4

SNP Enrichment and Detection

In some embodiments, the present techniques can be used to detect SNPs in a sample. Instead of initially amplifying a reaction mixture that contains both a majority nucleic acid sequence and a minority nucleic acid sequence, a known nucleic acid sequence (a control sequence, FNAS) that will form a heteroduplex with the target nucleic acid sequence is added to the sample (target sequence, SNAS). PCR is used to amplify the sample, the product is melted, and the control nucleic acid sequence allowed to reanneal to any target nucleic acid sequences in the sample. Following this, the nucleic acid sequences in the sample are circularized and a mismatch dependent enzyme is added to cleave any heteroduplexes. A BMNAS is ligated into the duplex and the BM is isolated from the initial solution. If the BMNAS is isolated with any additional nucleic acid sequence that matches the initial control sequence, then a SNP for the known sequence was present in the sample. The nucleic acid sequence associated with the BMNAS can be sequenced, as described in Example 2, to fully identify the SNP.

Example 5

Heteroduplex Mate Paired Library Construction Using Bead Based Method

Figure 11:
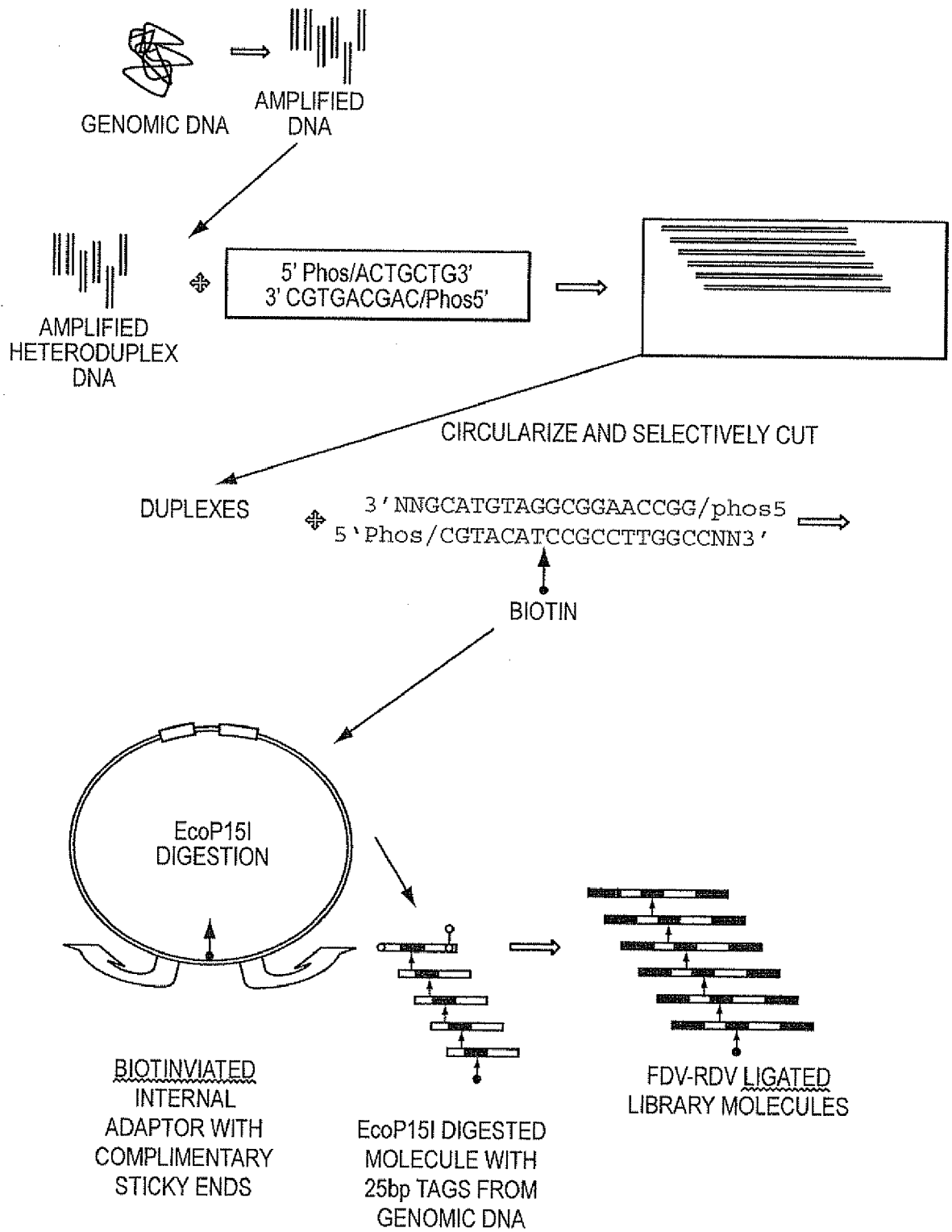
FIG. 11 depicts some of the relevant steps in creating a library of mismatched sequences, as described in Example 5.

To form a library of DNA sequences that are representative of the mismatches (e.g., variations in DNA sequences) present in a sample, one first PCR amplifies target regions and forms heteroduplexes of FNASs with SNASs. FIG. 11 provides a general outline of some of the steps in this Example. The other steps are further detailed above. The PCR mixture can include 10 pmol of each primer, 200 µm of each dNTP, 2 units of Amplitaq Gold® DNA polymerase (Applied Biosystems), 5 0 mM KCl, 1.5 mM $MgCl_2$, 10 mM Tris (pH 8.4), 0.01% gelatin, and 5-10 ng genomic DNA, for 100 µl of total reaction mixture. The mixture is then subject to 94° C. for 8 minutes to initiate a hotstart amplification and then 30 cycles of: 94° C. 2-minute, 60° C. 2-minute annealing, and 72° C. 2-minute polymerization. After the PCR amplification, the temperature can be set to 95° C. for 5 minutes and can be slow cooled to 4° C. at 3° C./minute to form heteroduplexes. Optionally, one can purify the DNA with non-enzymatic column or SPRI beads. (In some embodiments, residual Exo-SAP is to be avoided.)

Once the heteroduplexes are created, one then circularizes the homoduplexes and the heteroduplexes. This can be achieved by adding CAP linkers and circularizing via CAP ligation. Two CAP linker sequences can be used. The first sequence can be CAPA Sequence: /5Phos/ACTGCTG, and the second sequence can be CAPB Sequence: /5Phos/CAG-CAGGC. The reaction mixture can include 2 µl CAP linkers, 450 pmol/µl, 12 µl 5× Invitrogen Ligase Buffer, 3 µl Invitrogen HC ligase (5 U/µl), 15 µl End-Repaired DNA, and 31 µl dH2O. One then incubates the reaction overnight at 16° C.

One then PCl treats the ligation reaction samples and loads them onto a 1.2% Agarose gel in 1×TAE buffer. One then runs the gel for 2.5-3 hrs at 110V in 1×TAE buffer. One then takes a $2^{nd}$ cut for 2-3 kb sized genomic DNA with CAP likers ligated onto them. One then elutes the DNA from the Agarose gel using, for example, a Geneclean® purifying kit from Qbiogene (Irvine, Calif.).

One can calculate the amount of CAP linkers that can be used. Preferably, one uses an excess of CAP linkers, in some embodiments the CAP linker is present in at least a 100 fold amount. The relevant formulae are as follows:

1 µg×$10^6$ pg/µg×1 pmol/660 pg×½₅₀bp=6 pico moles 1.5 µg×6=9 pico moles

To get 100 fold of CAP linkers at least 900 pmoles can be used. One can also calculate the parameters for the circularization ligation reaction using the following formulae.

pmols DNA/µg size

µg DNA×(1,000,000 pg/µg)×(1 pmol/(660 pg/bp))× 1/# of bp=pmols

1 µg×$10^6$ pg/µg×1 pmol/660 pg×½₅₀₀bp=0.6 pico moles 5.0 µg×0.6 pico moles=3.0 pmoles To determine the parameters for achieving intra-molecular ligation, one can use the following formulae:

$J$=63.4 constant/square root (DNA size in kb)

$I$=($J$/percent intramolecular (0.95 for 95%))−$J$

I gives the µg/ml or ng/µl for the final concentration of the ligation. Based on the I value, the dilution of the ligation reaction can be decided. As calculated earlier 1 µg of 250 bp DNA fragments is 6 pmoles.

$J$=63.4/√2.5 63.4/1.58=40.1

$I$=40.1/0.90−40.1=4.6 ng/µl $I$=40.1/0.95−40.1=2.1 ng/µl $I$=40.1/0.98−40.1=0.8 ng/µl

The circularization reaction can be set up using 500 ng DNA, which is equivalent to 3 picomoles. Preferably one uses a 1:3 ratio (3 pmoles λ 0.25 kb: 9 pmoles T30 sticky internal adaptor). To get 95% or more circularization, a reaction that will dilute 5 μg of λ DNA to at least 2.1 ng/μl can be used.

Next, one can then cleaves the circularized heteroduplexes using EndoV. One can use 1 Unit of New England Biolabs (Ipswich, Mass.) Endonuclease V for each picomole of PCR product and incubate at 37° C. for 2 hrs in 1×NEBuffer 4, 20 mM Tris-Acetate, 50 mM K-Acetate, 10 mM Magnesium Acetate, and 1 mM DTT, at pH 7.9 at 25° C. One can then PCl precipitate the DNA and re-suspend in 33 μl of dH$_2$O to get a 100 ng/μl stock.

Next one can add the BMNAS to the solution that contains the duplexes (cut heteroduplexes). A biotin containing BMNAS can be used, having the following sequences StickyT30A Sequence: /5Phos/GGCCAAGGCGGATG-TACGNN (SEQ ID NO:1) and T30B biotin Sequence: /5Phos/CGT ACA/iBiodT/CCGCCTTGGCCNN (SEQ ID NO:2). Circularization conditions can be used. To avoid Internal adaptor concatenation RR, PP, PR, RP adaptors can be used in different wells. (R=Purine, P=Pyrimidine). The ligation reaction can include 15 μl EndoV treated PCR product or 500 ng of 300 bp PCR product, 180 μl 5× ligase buffer, 1.5 μl Sticky BioT30 (2 pmoles/μl), 4 μl HC ligase and 699.5 μl dH$_2$O. The mixture can be incubated over night at 16° C.

Following this, the un-circularized product can be removed by Plasmid-safe™ DNase treatment. 5 μl ATP and 5 μl ATP dependant Plasmid-safe™ Dnase can be added to each of the 3 tubes in order to remove substantially all of the un-circularized product. One then incubates for 40 minutes at room temperature and then heat kills for 20 minutes at 70° C. This can be followed with a PCl precipitation and resuspension of the product into 80 μl of dH$_2$O.

Following this, one can EcoP15I digest the -BioT30-circles, followed by PCl precipitation of the digestion product, a three fold wash, and resuspension in 70 μl dH$_2$O. The EcoP15I digestion can include 80 μl of circularized DNA, 16 μl NEB3 buffer (10×); 16 μl BSA (10×), 16 μl Sinefungin (50 μM), 16 μl ATP (10×), and 16 μl EcoP15I enzyme, for 160 μl of total volume. The solution can then be incubated at 37° C. for 1-2 hrs.

EcoP15I creates sticky ends and hence an end polishing step can be performed before ligation of the adapters. The polishing step can include the following: 70 μl digestion product, 10 μl 10× Epicentre® End-it Buffer, 10 μl Epicentre End-it ATP, 10 μl End-it dNTPs, and 2 μl of End-it Enzyme mix, incubated at room temperature for 40 minutes.

Following this, the repaired ends can be bound to beads. One can PCl treat the mixture after bringing the volume to 200 μl and then add 200 μl 2× binding Wash. One can then bind to pre washed M280 Streptavidin beads for 15 minutes (which can be washed by 1×W1E 1×, 1×BSA 1×, and 1×BiW 1×). After binding the End Repaired lambda-BioT30 EcoP15I digested product to the beads one can wash the product by 2×W1E (change tubes), 2×W1E (37° C.) (change tubes), 1×BiW 1× (change tubes) and 1×50 μl 1× Ligase buffer (change tubes).

Following this, one can ligate adaptors (in this case PCR priming sites) to the cut BMD (End Repaired lambda-BioT30 EcoP15I digested product). Two sets of adaptors can be used. FDV2A: CCA CTA CGC CTC CGC TTT CCT CTC TAT GGG CAG TCG GTG AT (SEQ ID NO:3), FDV2B: ATC ACC GAC TGC CTA TAG AGA GGA MG CGG AGG CGT AGT GGT T (SEQ ID NO:4) and RDV2A: CTG CCC CGG GTT CCT CAT TCT CT (SEQ ID NO:5); RDV2B: AGA GAA TGA GGA ACC CGG GGC AGT T (SEQ ID NO:6).

The reaction mixture can include 50 μl DNA bound beads in 1× Ligase buffer, 3.7 μl FDV (24 pmoles/μl), 3.7 μl RDV (24 pmoles/μl), and 3 μl HC ligase (5 U/μl) (Invitrogen). The mixture can be incubated at RT for 1.5 hrs. FDV is FDV2A and FDV2B annealed together and RDV is RDV2A and RDV2B annealed together. Following this, the product can be washed as follows: 2×W1E (37° C.) (change tubes), 2×W1E RT (change tubes), and 2×BiW 1×(change tubes). The mixture can be incubated at 65° C. for 15 minutes and then chilled on ice. The mixture can also be washed with 1×50 μl 1×NEB2 buffer and transferred to a fresh tube before proceeding to nick translation. The DNA can then be nick translated by using 39 μl DNA bound to beads in 1×NEB2 buffer, 0.8 μl 24 mM dNTP, and 1.5 μl DNA poll, incubated at 16° C. for 30 minutes.

Following this, the product can be amplified by PCR using Asymmetric Primers to the asymmetric priming sites. The first primer can be: AsymPrimerFDV2: CCA CTA CGC CTC CGC TTT CCT CTC TAT G (SEQ ID NO:7) and the second primer can be: AsymPrimerRDV2: CTG CCC CGG GTT CCT CAT TCT (SEQ ID NO:8). The reaction mixture can include 50 μl PCR supermix, 1 μl FDV2, and 1 μl RDV2. The PCR cycling program can include: 95° C. 5 minutes, [95° C. 15 sec; 62° C. 15 sec; 70° C. 1 minute]×35 cycles, 70° C. 5 minutes, and 4° C. forever. If the PCR looks good, a larger scale PCR with 2 μl PFU or any other high fidelity enzyme can be added to the reaction cocktail. Large scale PCR can be carried out using 1 μl template in 100 μl platinum Taq PCR supermix, one μl of FDV2, and one μl of RDV2 for 30 cycles. The product can then be QIA purified (Qiagen) and loaded on a PAGE gel to isolate the appropriate library band. The cut band can be eluted using a PAGE gel elution protocol and the eluted product can be QIA column purified. The product can be eluted in 100 μl of LoTE buffer and can be quantitated on nano drop to be 5 ng/μl.

This will provide one with a library of nucleic acid sequences that have asymmetric primers. The library will include nucleic acid sequences that were involved in the formation of heteroduplexes and involved a base pair mismatch. Thus, the library can contain all, some, or at least one nucleic acid sequence (e.g., a gene) that has a base pair mismatch from other nucleic acid sequences.

The following generally describes some of the above steps in more detail. "PCl" is a phenol-chloroform step in which one adds equal volumes phenol-chloroform to an enzyme reaction, spins for 5 minutes at room temperature, and then extracts the aqueous phase to a fresh tube. The Alcohol Precipitation involves adding 7.5M ammonium acetate to a final conc. of 3M, adding 100× Glycoblue™ glycogen (Ambion) to 1×, and adding 100% ice cold ethanol to a final concentration of 70% or 0.7 volumes of isopropyl alcohol at room temperature. One can then vortex, heat to 80° C. for 10 minutes, and spin at 4° C. if using ethanol or else spin at room temperature at 14000 rpm in microfuge for 15 min. One can then remove the supernatant, wash the pellet twice in ice cold 70% ethanol with large fragments, or ice cold 80% ethanol with fragments under 500 bp. Quantitation can be performed on nanodrop; however, when using Glycoblue™ glycogen, one can run a control ethanol precipitation with equal Glycoblue™ glycogen to serve as a blank. Glycoblue™ glyogen readings can be used as guidelines. If quantization is critical, the sample can be column purified before reading the sample.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method for the enrichment of a nucleic acid sequence, said method comprising:
   forming a heteroduplex comprising a first nucleic acid sequence and a second nucleic acid sequence, wherein said heteroduplex comprises at least one mismatched base pair between the first nucleic acid sequence and the second nucleic acid sequence;
   circularizing the heteroduplex to form a circularized heteroduplex (CHET);
   preferentially cutting the CHET to form a duplex using an enzyme that recognizes the mismatched base pair;
   ligating a binding moiety nucleic acid sequence (BMNAS) into the duplex to form a binding moiety duplex, wherein said BMNAS comprises: two nucleic acid sequences hybridized to one another and a binding moiety; and
   selecting the binding moiety by using a purifying moiety to bind to the binding moiety, thereby enriching the second nucleic acid sequence.

2. The method of claim 1, wherein the preferential cutting occurs at a predetermined location relative to the mismatched base pair.

3. The method of claim 2, wherein Endo V is used to cut the CHET.

4. The method of claim 1, wherein the preferential cutting occurs at a location one base pair away from the mismatched base pair.

5. The method of claim 1, further comprising forming a nucleic acid homoduplex and circularizing the homoduplex to form a circularized homoduplex (CHOM), wherein the CHOM does not contain a mismatched base pair, and wherein said forming and circularizing of the homoduplex is performed together with the forming and circularizing of the heteroduplex.

6. The method of claim 5, wherein the step of preferentially cutting the CHET does not result in a significant cutting of the CHOM.

7. The method of claim 1, wherein the BMNAS further comprises a first restriction site.

8. The method of claim 7, wherein the BMNAS further comprises a second restriction site and wherein each of the restriction sites is located at opposite ends of the nucleic acid sequence.

9. The method of claim 1, wherein the binding moiety comprises biotin.

10. The method of claim 1, wherein more than one type of BMNAS is used, and wherein the BMNASs have degenerate 5' and 3' ends.

11. The method of claim 2, wherein at least 16 BMNASs are used, each BMNAS having a different 5' and 3' end sequence combination.

12. The method of claim 11, wherein at least 1024 BMNASs are used, each BMNAS having a different 5' and 3' end sequence combination.

13. The method of claim 1, further comprising the step of cutting the binding moiety duplex to form a cut binding moiety duplex (CBMD).

14. The method of claim 13, wherein the cutting is controlled by restriction sites within the BMNAS.

15. The method of claim 14, wherein the cutting occurs by a Type IIs or a Type III cutter.

16. The method of claim 15, wherein the cutting occurs approximately 30 base pairs away from a restriction site for the cutting.

17. The method of claim 13, further comprising the step of identifying the second nucleic acid sequence.

18. The method of claim 13, further comprising the step of identifying the mismatched base pair.

19. The method of claim 18, wherein said identification occurs by sequencing the mismatched base pair.

20. The method of claim 13, further comprising the step of adding a first adapter to a first end of the CBMD.

21. The method of claim 20, further comprising the step of adding a second adapter to a second end of the CBMD, wherein the first and second adapters are not the same.

22. The method of claim 21, wherein the first adapter is a first primer site and the second adapter is a second primer site.

23. The method of claim 22, further comprising the step of using the first and second primer sites to amplify a sequence between the two primer sites.

24. The method of claim 23, wherein the amplification is achieved through emulsion PCR.

25. The method of claim 23, further comprising the step of sequencing the amplified sequence.

26. The method of claim 1, wherein the method is performed in vitro.

27. The method of claim 1, wherein the enrichment of the second nucleic acid sequence occurs only through the binding of the binding moiety to the purifying moiety.

28. The method of claim 1, further comprising the step of forming a second CHET, wherein the first CHET and the second CHET have different mismatched base pairs.

29. The method of claim 28, wherein at least 100 CHETs are formed, each with a different mismatched base pair.

30. The method of claim 29, wherein at least 1000 CHETs are formed, each with a different mismatched base pair.

31. The method of claim 1, wherein the first nucleic acid comprises DNA.

32. The method of claim 1, wherein the second nucleic acid comprises DNA.

33. The method of claim 1, wherein there is more of the first nucleic acid sequence than the second nucleic acid sequence during the formation of the heteroduplex.

34. The method of claim 1, wherein the ratio of first to second nucleic acid sequences present during the formation of the heteroduplex is no less than 5:1.

35. The method of claim 1, wherein the ratio of first to second nucleic acid sequences present during the formation of the heteroduplex is no less than 100:1.

36. The method of claim 1, wherein the ratio of first to second nucleic acid sequences present during the formation of the heteroduplex is no less than 1000:1.

37. A method for the enrichment of a nucleic acid sequence, said method comprising:
providing a sample containing a first nucleic acid sequence (FNAS) as well as a second nucleic acid sequence (SNAS);
providing two primers suitable for hybridization on complementary strands of the FNAS and the SNAS;
providing a polymerase;
combining the sample, the primers, and the polymerase to form a polymerase chain reaction mixture;
subjecting the polymerase chain reaction mixture to one or more polymerase chain reaction cycles to create a polymerase chain reaction extension product;
denaturing the polymerase chain reaction extension product to separate a FNAS and a SNAS;
annealing the polymerase chain reaction extension product to form a heteroduplex comprising the FNAS and the SNAS and to form a homoduplex comprising the FNAS;
circularizing the heteroduplex to form a circularized heteroduplex (CHET);
circularizing the homoduplex to form a circularized homoduplex (CHOM);
providing an endonuclease that preferentially cuts the heteroduplex at a location one base away from mismatched base pairs, wherein said cutting of the heteroduplex is preferential over the cutting of the homoduplex;
combining the CHET, the CHOM, and the endonuclease to form an endonuclease cleavage reaction mixture;
incubating the endonuclease cleavage reaction mixture so that the endonuclease preferentially cuts the CHET at a location one base away from a mismatched base pairs;
providing a plurality of binding moiety nucleic acid sequences (BMNAS), wherein said BMNASs comprise:
a double stranded nucleic acid sequence;
biotin associated with the double stranded nucleic acid sequence,
two EcoP15I restriction sites on each nucleic acid sequence, wherein one restriction site is located near or at the 3' end of one nucleic acid strand and the second restriction site is located near or at the 5' end of the same nucleic acid strand, and
degenerate ends on each end of each nucleic acid sequence;
ligating the BMNAS into the duplex to form a binding moiety duplex;
cutting the binding moiety duplex using EcoP15I;
concentrating the binding moiety duplex by using magnetic beads;
cutting the concentrated binding moiety duplex by using EcoP15I to form a cut binding moiety duplex (CBMD);
adding a first adapter to a first end of the CBMD;
adding a second adapter to a second end of the CBMD, wherein the first and second adapters are different;
performing emulsion PCR to amplify the CBMD using the first and second adapters as priming sites; and
performing highly parallel non-electrophoretic sequencing technique on the CBMD to identify the mismatched base pair.

* * * * *